United States Patent
Facchini

(10) Patent No.: US 10,227,353 B2
(45) Date of Patent: Mar. 12, 2019

(54) COMPOSITIONS AND METHODS FOR MAKING ALKALOID MORPHINANS

(71) Applicant: EPIMERON INC., Calgary (CA)

(72) Inventor: Peter James Facchini, Calgary (CA)

(73) Assignee: Epimeron Inc., Calgary, Alberta (CA)

( * ) Notice: Subject to any disclaimer, the term of this patent is extended or adjusted under 35 U.S.C. 154(b) by 0 days.

(21) Appl. No.: 15/505,625

(22) PCT Filed: Aug. 21, 2015

(86) PCT No.: PCT/CA2015/050796
§ 371 (c)(1),
(2) Date: Feb. 22, 2017

(87) PCT Pub. No.: WO2016/026048
PCT Pub. Date: Feb. 25, 2016

(65) Prior Publication Data
US 2017/0267686 A1 Sep. 21, 2017

Related U.S. Application Data

(60) Provisional application No. 62/040,754, filed on Aug. 22, 2014.

(51) Int. Cl.
*C07D 489/02* (2006.01)
*C12N 9/90* (2006.01)
*C07D 489/08* (2006.01)
*C12N 9/04* (2006.01)
*C12P 17/18* (2006.01)

(52) U.S. Cl.
CPC ......... *C07D 489/02* (2013.01); *C07D 489/08* (2013.01); *C12N 9/0006* (2013.01); *C12N 9/90* (2013.01); *C12P 17/18* (2013.01); *C12P 17/188* (2013.01); *C12Y 101/01247* (2013.01)

(58) Field of Classification Search
CPC ..... C07D 489/02; C07D 489/08; C12P 17/18; C12P 17/188; C12Y 101/01247
See application file for complete search history.

(56) References Cited

U.S. PATENT DOCUMENTS 2,797,222 A 6/1957 Conroy
2014/0115737 A1 4/2014 Abad

FOREIGN PATENT DOCUMENTS

WO 2014143744 A2 9/2014

OTHER PUBLICATIONS

Walker, Tetrahedron, vol. 60, 2004, 561-568. (Year: 2004).*
Fleischhacker, ARKIVOC 2001, (ii) 82-94. (Year: 2001).*
Meuzelaar, CA 120:134883 abstract only of Requeil des Travaux Chimiques des Pays-Bas, 112(11), 573-577, 1993. (Year: 1993).*
Larkin, P. et al., "Increasing morphinan alkaloid production by over-expressing codeinone reductase in transgenic Papaver somniferum", Plant Biotechnology Journal, 2007, vol. 5, p. 26-37.
Lenz, R. et al. "Stereoselective Reduction of Codeinone, the Penultimate Enzymic Step During Morphine Biosynthesis in Papaver somniferum", Tetrahedron Letters, Elsevier, Amsterdam, NL, vol. 36, No. 14, p. 2449-2452, Apr. 3, 1995.

* cited by examiner

*Primary Examiner* — D Margaret M Seaman
(74) *Attorney, Agent, or Firm* — Bereskin & Parr LLP/S.E.N.C.R.L., s.r.l.; Micheline Gravelle

(57) ABSTRACT

Methods that may be used for the manufacture of a class of chemical compounds known as morphinans, including neopine, are provided. Compositions useful for the synthesis of morphinans, including neopine, are also provided.

6 Claims, 15 Drawing Sheets

Specification includes a Sequence Listing.

```
          .........10.........20.........30.........40.........50
COR1.3    MESNGVPMIT LSSGIRMPAL GMGTAETMVK GTEREKLAFL KAIEVGYRHF
CDI       MESNGVPMIT LSSGIRMPAL GMGTVETMEK GTEREKLAFL KAIEVGYRHF

.........60.........70.........80.........90........100
COR1.3    DTAAAYQSEE CLGEAIAEAL QLGLIKSRDE LFITSKLWCA DAHADLVLPA
CDI       DTAAAYQTEE CLGEAIAEAL QLGLIKSRDE LFITSKLWCA DAHADLVLPA

........110........120........130........140........150
COR1.3    LQNSLRNLKL DYLDLYLIHH PVSLKPGKFV NEIPKDHILP MDYKSVWAAM
CDI       LQNSLRNLKL DYLDLYLIHH PVSLKPGKFV NEIPKDHILP MDYKSVWAAM

........160........170........180........190........200
COR1.3    EECQTLGFTR AIGVCNFSCK KLQELMAAAK IPPVVNQVEM SPTLHQKNLR
CDI       EECQTLGFTR AIGVCNFSCK KLQELMATAN SPPVVNQVEM SPTLHQKNLR

........210........220........230........240........250
COR1.3    EYCKANNIMI TAHSVLGAIC APWGSNAVMD SKVLHQIAVA RGKSVAQVSM
CDI       EYCKANNIMI TAHSVLGAVG AAWGTNAVMH SKVLHQIAVA RGKSVAQVSM

........260........270........280........290........300
COR1.3    RWVYQQGASL VVKSFNEGRM KENLKIFDWE LTAENMEKIS EIPQSRTSSA
CDI       RWVYQQGASL VVKSFNEARM KENLKIFDWE LTAEDMEKIS EIPQSRTSSA

........310........320
COR1.3    DFLLSPTGPF KTEEEFWDEK D
CDI       AFLLSPTGPF KTEEEFWDGE V
```

FIGURE 6

SEQUENCE LISTING

```
<160> NUMBER OF SEQ ID NOS: 22

<210> SEQ ID NO 1
<211> LENGTH: 966
<212> TYPE: DNA
<213> ORGANISM: Papaver somniferum

<400> SEQUENCE: 1
atggagagta atggtgttcc tatgattact ctcagttccg gcattcggat gcctgcttta      60
ggtatgggaa cagttgaaac aatggaaaag ggaactgaaa gagagaaatt ggcgttttg     120
```

```
aaagcgatag aggtcggtta cagacacttc gatacagctg ctgcatacca aactgaagag    180
tgtcttggtg aagctatagc tgaagcactt caacttggtc taataaaatc tcgagatgaa    240
ctcttcatca cttccaagct ctggtgcgct gatgctcacg ctgatcttgt cctccctgct    300
cttcagaatt ctctgaggaa tctcaaattg gactatcttg atctatattt gatacaccat    360
ccggtaagct tgaagccagg gaagtttgtt aacgaaatac aaaggatca tatccttcca    420 atggactaca atctgtatg gcagccatg gaagagtgtc agacccttgg cttcactagg    480
gcaatcgggg tctgtaattt ctcatgcaaa aagcttcaag agttgatggc aacagccaac    540
agccctccag ttgtgaatca agtggagatg agcccgactt acatcaaaa aaatctgagg    600 gaatattgca aggccaataa tatcatgatc accgcacact cagttttggg agccgtaggt    660
gccgcctggg gcaccaatgc agttatgcat tctaaggtgc ttcaccagat tgctgtggcc    720
agaggaaaat ctgttgccca ggttagtatg agatgggttt accagcaagg cgcgagtctt    780
gtggtgaaaa gtttcaatga agcgaggatg aaggaaaacc ttaagatatt tgattgggaa    840
ctaacggcag aagacatgga aaagatcagt gagattccac aatctagaac aagctctgct    900
gctttcttgt tatcaccgac tggaccttc aaaactgaag aagagttctg ggacggagaa    960
gtttga                                                               966

<210> SEQ ID NO 2
<211> LENGTH: 321
<212> TYPE: PRT
<213> ORGANISM: Papaver somniferum

<400> SEQUENCE: 2

Met Glu Ser Asn Gly Val Pro Met Ile Thr Leu Ser Ser Gly Ile Arg
1               5                   10                  15

Met Pro Ala Leu Gly Met Gly Thr Val Glu Thr Met Glu Lys Gly Thr
            20                  25                  30

Glu Arg Glu Lys Leu Ala Phe Leu Lys Ala Ile Glu Val Gly Tyr Arg
        35                  40                  45

His Phe Asp Thr Ala Ala Ala Tyr Gln Thr Glu Glu Cys Leu Gly Glu
    50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Ala Asp Ala His Ala Asp Leu
                85                  90                  95

Val Leu Pro Ala Leu Gln Asn Ser Leu Arg Asn Leu Lys Leu Asp Tyr
            100                 105                 110

Leu Asp Leu Tyr Leu Ile His His Pro Val Ser Leu Lys Pro Gly Lys
        115                 120                 125

Phe Val Asn Glu Ile Pro Lys Asp His Ile Leu Pro Met Asp Tyr Lys
    130                 135                 140

Ser Val Trp Ala Ala Met Glu Glu Cys Gln Thr Leu Gly Phe Thr Arg
145                 150                 155                 160

Ala Ile Gly Val Cys Asn Phe Ser Cys Lys Lys Leu Gln Glu Leu Met
                165                 170                 175

Ala Thr Ala Asn Ser Pro Pro Val Val Asn Gln Val Glu Met Ser Pro
            180                 185                 190

Thr Leu His Gln Lys Asn Leu Arg Glu Tyr Cys Lys Ala Asn Asn Ile
        195                 200                 205

Met Ile Thr Ala His Ser Val Leu Gly Ala Val Gly Ala Ala Trp Gly
    210                 215                 220
```

```
Thr Asn Ala Val Met His Ser Lys Val Leu His Gln Ile Ala Val Ala
225                 230                 235                 240

Arg Gly Lys Ser Val Ala Gln Val Ser Met Arg Trp Val Tyr Gln Gln
            245                 250                 255

Gly Ala Ser Leu Val Val Lys Ser Phe Asn Glu Ala Arg Met Lys Glu
        260                 265                 270

Asn Leu Lys Ile Phe Asp Trp Glu Leu Thr Ala Glu Asp Met Glu Lys
    275                 280                 285

Ile Ser Glu Ile Pro Gln Ser Arg Thr Ser Ser Ala Ala Phe Leu Leu
    290                 295                 300

Ser Pro Thr Gly Pro Phe Lys Thr Glu Glu Glu Phe Trp Asp Gly Glu
305                 310                 315                 320

Val
```

<210> SEQ ID NO 3
<211> LENGTH: 1035
<212> TYPE: DNA
<213> ORGANISM: Papaver somniferum
<220> FEATURE:
<221> NAME/KEY: misc_feature
<223> OTHER INFORMATION: COR1.1

<400> SEQUENCE: 3

```
gaaaaatgga gagtaatggt gtacctatga tcactctcag ttccggcatt cggatgcctg      60
ctttaggtat gggaacagct gaaacaatgg taaaaggaac agaaagagag aaattggcgt    120
ttttgaaagc gatagaggtc ggttacagac acttcgatac agctgctgca taccaaactg    180
aagagtgtct tggtgaagct atagctgaag cacttcaact tggtctaata aaatctcgag    240
atgaactctt catcacttcc aagctctggt gcgctgatgc tcacgctgat cttgtcctcc    300
ctgctcttca gaattctctg aggaatctta aattggacta tcttgatcta tatttgatac    360
accatccggt aagcttgaag ccagggaagt tgttaacga aataccaaag gatcatatcc     420
ttccaatgga ctacaaatct gtatgggcag ccatggaaga gtgtcagacc cttggcttca    480
ctagggcaat cggggtctgt aatttctcat gcaaaaggct tcaagagttg atggaaacag    540
ccaacagccc tccagttgtg aatcaagtgg agatgagccc gactttacat caaaaaaatc    600
tgagggaata ttgcaaggcc aataatatca tgatcaccgc acactcagtt ttgggagccg    660
taggtgccgc ctggggcacc aatgcagtta tgcattctaa ggtgcttcac cagattgctg    720
tggccagagg aaaatctgtt gcccaggtta gtatgagatg ggtttaccag caaggcgcga    780
gtcttgtggt gaaaagtttc aatgaagcga ggatgaagga aaaccttaag atatttgatt    840
gggaactaac ggcagaagac atggaaaaga tcagtgagat tccacaatct agaacaagct    900
ctgctgcttt cttgttatca ccgactggac ctttcaaaac tgaagaagag ttctgggatg    960
agaaggattg aaacatcaat tatagatggt aagtgaggac tgtcaaaaaa gtaatcagtt   1020
tttccctccg ttttg                                                    1035
```

<210> SEQ ID NO 4
<211> LENGTH: 966
<212> TYPE: DNA
<213> ORGANISM: Papaver somniferum
<220> FEATURE:
<221> NAME/KEY: misc_feature
<223> OTHER INFORMATION: COR1.2

<400> SEQUENCE: 4

```
atggagagta atggtgtacc tatgatcact ctcagttccg gcattcggat gcctgcttta      60
ggtatgggaa cagttgaaac aatggaaaag gaacagaaa gagagaaatt ggcgttttg      120
aatgcgatag aggtcggtta cagacacttc gatacagctg ctgcatacca aagtgaagag     180
tgtcttggtg aagctatagc tgaagcactt caacttggtt taataaaatc tcgagatgaa     240
ctcttcatca cttccaagct ctggtgcgct gatgctcacg ctgatcttgt cctccctgct     300
cttcagaatt ctctgaggaa tctcaaattg gagtaccttg atctatattt gatacaccat     360
ccggtaagct tgaagccagg gaagcttgtt aacgaaatac caaaggatca tattcttcca     420
atggactaca atctgtatg gcagccatg gaagagtgtc agacccttgg cttcactagg      480
gcaatcggtg tcagtaattt ctcatgcaaa aagcttcaag agttgatggc aacagccaag     540
atccctccag ttgtgaatca agtggagatg agcccgactt acatcaaaaa aaatctgagg    600
gaatattgca aggccaataa tatcatgatc actgcacact cggttttggg agccataggt     660
gctccatggg gcagcaacgc agttatggat tctaaggtgc ttcaccagat tgctgtggca     720
agaggaaaat ctgttgccca ggttagtatg agatgggttt accagcaagg cgcgagtctt     780
gtggtgaaaa gtttcaatga agcgaggatg aaggaaaacc ttaagatatt tgattcggaa    840
ctaacggcag aagatatgga aaagatcagt gagattccgc aatctagaac aagctctgct     900
gatttcttgt tatcaccgac tggacccttc aaaactgaag aagagttctg ggatgagaag    960
gattga                                                             966
```

<210> SEQ ID NO 5  
<211> LENGTH: 966  
<212> TYPE: DNA  
<213> ORGANISM: Papaver somniferum  
<220> FEATURE:  
<221> NAME/KEY: misc_feature  
<223> OTHER INFORMATION: COR1.3

<400> SEQUENCE: 5

```
atggagagta atggtgtacc tatgatcact ctcagttccg gcattcggat gcctgcttta      60
ggtatgggaa cagctgaaac aatggtaaaa ggaacagaaa gagagaaatt ggcgttttg      120
aaagcgatag aggtcggtta cagacacttc gatacagctg ctgcatacca aagtgaagag     180
tgtcttggtg aagctatagc tgaagcactt caacttggtc taataaaatc tcgagatgaa     240
ctcttcatca cttccaagct ctggtgcgct gatgctcacg ctgatcttgt cctccctgct     300
cttcagaatt ctctgaggaa tcttaaattg gactatcttg atctatattt gatacaccat     360
ccggtaagct tgaagccagg gaagtttgtt aacgaaatac caaaggatca tatccttcca     420
atggactaca atctgtatg gcagccatg gaagagtgtc agacccttgg cttcactagg      480
gcaatcgggg tctgtaattt ctcatgcaaa aagcttcaag agttgatggc agcagccaag     540
atccctccag ttgtgaatca agtggagatg agcccgactt acatcaaaaa aaatctgagg    600
gaatattgca aggccaataa tatcatgatc actgcacact cggttttggg agccatatgt     660
gctccatggg gcagcaatgc agttatggat tctaaggtgc ttcaccagat tgctgtggca     720
agaggaaaat ctgttgccca ggttagtatg agatgggttt accagcaagg cgcgagtcta     780
gtggtgaaaa gtttcaatga agggaggatg aaggaaaacc ttaagatatt tgattgggaa    840
ctaacggcag agaatatgga aaagatcagt gagattccgc aatctagaac aagctctgct     900
```

```
gatttcttgt tatcaccgac tggacctttc aaaactgaag aagagttctg ggatgagaag   960
gattga                                                              966
```

<210> SEQ ID NO 6
<211> LENGTH: 966
<212> TYPE: DNA
<213> ORGANISM: Papaver somniferum
<220> FEATURE:
<221> NAME/KEY: misc_feature
<223> OTHER INFORMATION: COR1.4

<400> SEQUENCE: 6

```
atggagagta atggtgtacc tatgatcact ctcagttccg gcattcggat gcctgcttta    60
ggtatgggaa cagctgaaac aatggtaaaa ggaacagaaa gagagaaatt ggcgttttg    120 aaagcgatag aggtcggtta cagacacttc gatacagctg ctgcatacca agtgaagag    180 tgtcttggtg aagctatagc tgaagcactt caacttggtt aataaaatc tcgagatgaa    240 ctcttcatca cttccaagct ctggtgcgct gatgctcacg ctgatcttgt cctccctgct    300
cttcagaatt ctctgaggaa tctcaaattg gagtatcttg atctatattt gatacaccat    360
ccggtaagct tgaagccagg gaaatttgtt aacgaaatac caaaggatca tattcttcca    420
atggactaca atctgtatg gcagccatg aagagtgtc agacccttgg cttcactagg      480
gcaatcggtg tcagtaattt ctcatgcaaa aagcttcaag agttgatggc agcagccaag    540
atccctccag ttgtgaatca gtggagatg agccctactt acatcaaaa aaatctgagg     600 gaatattgca aggccaataa tatcatgatc actgcacact cggttttggg agccataggt    660
gctccatggg gcagcaatgc agttatggat tctaaggtgc ttcaccagat tgctgtggca    720
agaggaaaat ctgttgccca ggttagtatg agatgggttt accagcaagg cgcgagtctt   780
gtggtgaaaa gtttcaatga agggaggatg aaggaaaacc ttaagatatt tgattgggaa    840
ctaacggcag aagatatgga aaagatcagt gagattccgc aatctagaac aagctctgct    900
gctttcttgt tatcaccgac tggacctttc aaaactgaag aagagttctg ggatgagaag    960
gattga                                                              966
```

<210> SEQ ID NO 7
<211> LENGTH: 966
<212> TYPE: DNA
<213> ORGANISM: Papaver somniferum
<220> FEATURE:
<221> NAME/KEY: misc_feature
<223> OTHER INFORMATION: COR1.5

<400> SEQUENCE: 7

```
atggagagta atggtgttcc tatgattact ctcagttccg gcattcggat gcctgcttta    60
ggtatgggaa cagttgaaac aatggaaaaa ggaactgaaa gagagaaatt ggcgttttg    120 aaagcgatag aggtcggtta cagacacttc gatacagctg ctgcatacca aactgaagag    180
tgtcttggtg aagctatagc tgaagcactt caacttggtc aataaaatc tcgagatgaa    240 ctcttcatca cttccaagct ctggtgcgct gatgctcacg ctgatcttgt cctccctgct    300
cttcagaatt ctctgaggaa tctcaaattg gactatcttg atctatattt gatacaccat    360
ccggtaagct tgaagccagg gaagtttgtt aacgaaatac cgaaggatca tatccttcca    420
atggactaca atctgtatg gcagccatg aagagtgtc agacccttgg cttcactagg      480
gcaatcgggg tctgtaattt ctcatgcaaa aagcttcaag agttgatggc aacagccaac    540
agccctccag ttgtgaatca gtggagatg agcccgactt acatcaaaa aaatctgagg     600
```

```
gaatattgca aggccaataa tatcatgatc accgcacact cagttttggg agccgtaggt    660
gccgcctggg gcaccaaagc agttatgcat tctaaggtgc ttcaccagat tgctgtggcc    720
agaggaaaat ctgttgccca ggttagtatg agatgggttt accagcaagg cgcgagtctt    780
gtggtgaaaa gtttcaatga agcgaggatg aaggaaaacc ttaagatatt tgattgggaa    840
ctaacggcag aagacatgga aaagatcagt gagattccac aatctagaac aagctctgct    900
gctttcttgt tatcaccgac tggacctttc aaaactgaag aagagttctg ggatgagaag    960
gattga                                                              966
```

<210> SEQ ID NO 8
<211> LENGTH: 321
<212> TYPE: PRT
<213> ORGANISM: Papaver somniferum
<220> FEATURE:
<221> NAME/KEY: MISC_FEATURE
<223> OTHER INFORMATION: COR1.1

<400> SEQUENCE: 8

```
Met Glu Ser Asn Gly Val Pro Met Ile Thr Leu Ser Ser Gly Ile Arg
1               5                   10                  15

Met Pro Ala Leu Gly Met Gly Thr Ala Glu Thr Met Val Lys Gly Thr
            20                  25                  30

Glu Arg Glu Lys Leu Ala Phe Leu Lys Ala Ile Glu Val Gly Tyr Arg
        35                  40                  45

His Phe Asp Thr Ala Ala Ala Tyr Gln Thr Glu Glu Cys Leu Gly Glu
    50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Ala Asp Ala His Ala Asp Leu
                85                  90                  95

Val Leu Pro Ala Leu Gln Asn Ser Leu Arg Asn Leu Lys Leu Asp Tyr
            100                 105                 110

Leu Asp Leu Tyr Leu Ile His His Pro Val Ser Leu Lys Pro Gly Lys
        115                 120                 125

Phe Val Asn Glu Ile Pro Lys Asp His Ile Leu Pro Met Asp Tyr Lys
    130                 135                 140

Ser Val Trp Ala Ala Met Glu Glu Cys Gln Thr Leu Gly Phe Thr Arg
145                 150                 155                 160

Ala Ile Gly Val Cys Asn Phe Ser Cys Lys Arg Leu Gln Glu Leu Met
                165                 170                 175

Glu Thr Ala Asn Ser Pro Pro Val Val Asn Gln Val Glu Met Ser Pro
            180                 185                 190

Thr Leu His Gln Lys Asn Leu Arg Glu Tyr Cys Lys Ala Asn Asn Ile
        195                 200                 205

Met Ile Thr Ala His Ser Val Leu Gly Ala Val Gly Ala Ala Trp Gly
    210                 215                 220

Thr Asn Ala Val Met His Ser Lys Val Leu His Gln Ile Ala Val Ala
225                 230                 235                 240

Arg Gly Lys Ser Val Ala Gln Ser Met Arg Trp Val Tyr Gln Gln
                245                 250                 255

Gly Ala Ser Leu Val Val Lys Ser Phe Asn Glu Ala Arg Met Lys Glu
            260                 265                 270

Asn Leu Lys Ile Phe Asp Trp Glu Leu Thr Ala Glu Asp Met Glu Lys
        275                 280                 285
```

```
Ile Ser Glu Ile Pro Gln Ser Arg Thr Ser Ser Ala Ala Phe Leu Leu
    290                 295                 300

Ser Pro Thr Gly Pro Phe Lys Thr Glu Glu Phe Trp Asp Glu Lys
305                 310                 315                 320

Asp

<210> SEQ ID NO 9
<211> LENGTH: 321
<212> TYPE: PRT
<213> ORGANISM: Papaver somniferum
<220> FEATURE:
<221> NAME/KEY: MISC_FEATURE
<223> OTHER INFORMATION: COR1.2

<400> SEQUENCE: 9

Met Glu Ser Asn Gly Val Pro Met Ile Thr Leu Ser Ser Gly Ile Arg
1               5                   10                  15

Met Pro Ala Leu Gly Met Gly Thr Val Glu Thr Met Glu Lys Gly Thr
            20                  25                  30

Glu Arg Glu Lys Leu Ala Phe Leu Asn Ala Ile Glu Val Gly Tyr Arg
        35                  40                  45

His Phe Asp Thr Ala Ala Ala Tyr Gln Ser Glu Glu Cys Leu Gly Glu
    50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Ala Asp Ala His Ala Asp Leu
                85                  90                  95

Val Leu Pro Ala Leu Gln Asn Ser Leu Arg Asn Leu Lys Leu Glu Tyr
            100                 105                 110

Leu Asp Leu Tyr Leu Ile His His Pro Val Ser Leu Lys Pro Gly Lys
        115                 120                 125

Leu Val Asn Glu Ile Pro Lys Asp His Ile Leu Pro Met Asp Tyr Lys
    130                 135                 140

Ser Val Trp Ala Ala Met Glu Glu Cys Gln Thr Leu Gly Phe Thr Arg
145                 150                 155                 160

Ala Ile Gly Val Ser Asn Phe Ser Cys Lys Lys Leu Gln Glu Leu Met
                165                 170                 175

Ala Thr Ala Lys Ile Pro Pro Val Val Asn Gln Val Glu Met Ser Pro
            180                 185                 190

Thr Leu His Gln Lys Asn Leu Arg Glu Tyr Cys Lys Ala Asn Asn Ile
        195                 200                 205

Met Ile Thr Ala His Ser Val Leu Gly Ala Ile Gly Ala Pro Trp Gly
    210                 215                 220

Ser Asn Ala Val Met Asp Ser Lys Val Leu His Gln Ile Ala Val Ala
225                 230                 235                 240

Arg Gly Lys Ser Val Ala Gln Val Ser Met Arg Trp Val Tyr Gln Gln
                245                 250                 255

Gly Ala Ser Leu Val Val Lys Ser Phe Asn Glu Ala Arg Met Lys Glu
            260                 265                 270

Asn Leu Lys Ile Phe Asp Ser Glu Leu Thr Ala Glu Asp Met Glu Lys
        275                 280                 285

Ile Ser Glu Ile Pro Gln Ser Arg Thr Ser Ser Ala Asp Phe Leu Leu
    290                 295                 300
```

Ser Pro Thr Gly Pro Phe Lys Thr Glu Glu Glu Phe Trp Asp Glu Lys
305                 310                 315                 320

Asp

<210> SEQ ID NO 10
<211> LENGTH: 321
<212> TYPE: PRT
<213> ORGANISM: Papaver somniferum
<220> FEATURE:
<221> NAME/KEY: MISC_FEATURE
<223> OTHER INFORMATION: COR1.3

<400> SEQUENCE: 10

Met Glu Ser Asn Gly Val Pro Met Ile Thr Leu Ser Ser Gly Ile Arg
1               5                   10                  15

Met Pro Ala Leu Gly Met Gly Thr Ala Glu Thr Met Val Lys Gly Thr
                20                  25                  30

Glu Arg Glu Lys Leu Ala Phe Leu Lys Ala Ile Glu Val Gly Tyr Arg
            35                  40                  45

His Phe Asp Thr Ala Ala Ala Tyr Gln Ser Glu Glu Cys Leu Gly Glu
        50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Ala Asp Ala His Ala Asp Leu
                85                  90                  95

Val Leu Pro Ala Leu Gln Asn Ser Leu Arg Asn Leu Lys Leu Asp Tyr
                100                 105                 110

Leu Asp Leu Tyr Leu Ile His His Pro Val Ser Leu Lys Pro Gly Lys
            115                 120                 125

Phe Val Asn Glu Ile Pro Lys Asp His Ile Leu Pro Met Asp Tyr Lys
        130                 135                 140

Ser Val Trp Ala Ala Met Glu Glu Cys Gln Thr Leu Gly Phe Thr Arg
145                 150                 155                 160

Ala Ile Gly Val Cys Asn Phe Ser Cys Lys Lys Leu Gln Glu Leu Met
                165                 170                 175

Ala Ala Ala Lys Ile Pro Pro Val Val Asn Gln Val Glu Met Ser Pro
                180                 185                 190

Thr Leu His Gln Lys Asn Leu Arg Glu Tyr Cys Lys Ala Asn Asn Ile
            195                 200                 205

Met Ile Thr Ala His Ser Val Leu Gly Ala Ile Cys Ala Pro Trp Gly
        210                 215                 220

Ser Asn Ala Val Met Asp Ser Lys Val Leu His Gln Ile Ala Val Ala
225                 230                 235                 240

Arg Gly Lys Ser Val Ala Gln Val Ser Met Arg Trp Val Tyr Gln Gln
                245                 250                 255

Gly Ala Ser Leu Val Val Lys Ser Phe Asn Glu Gly Arg Met Lys Glu
                260                 265                 270

Asn Leu Lys Ile Phe Asp Trp Glu Leu Thr Ala Glu Asn Met Glu Lys
            275                 280                 285

Ile Ser Glu Ile Pro Gln Ser Arg Thr Ser Ser Ala Asp Phe Leu Leu
        290                 295                 300

Ser Pro Thr Gly Pro Phe Lys Thr Glu Glu Glu Phe Trp Asp Glu Lys
305                 310                 315                 320

Asp

```
<210> SEQ ID NO 11
<211> LENGTH: 321
<212> TYPE: PRT
<213> ORGANISM: Papaver somniferum
<220> FEATURE:
<221> NAME/KEY: MISC_FEATURE
<223> OTHER INFORMATION: COR1.4

<400> SEQUENCE: 11

Met Glu Ser Asn Gly Val Pro Met Ile Thr Leu Ser Ser Gly Ile Arg
1               5                   10                  15

Met Pro Ala Leu Gly Met Gly Thr Ala Glu Thr Met Val Lys Gly Thr
            20                  25                  30

Glu Arg Glu Lys Leu Ala Phe Leu Lys Ala Ile Glu Val Gly Tyr Arg
        35                  40                  45

His Phe Asp Thr Ala Ala Ala Tyr Gln Ser Glu Glu Cys Leu Gly Glu
    50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Ala Asp Ala His Ala Asp Leu
                85                  90                  95

Val Leu Pro Ala Leu Gln Asn Ser Leu Arg Asn Leu Lys Leu Glu Tyr
            100                 105                 110

Leu Asp Leu Tyr Leu Ile His His Pro Val Ser Leu Lys Pro Gly Lys
        115                 120                 125

Phe Val Asn Glu Ile Pro Lys Asp His Ile Leu Pro Met Asp Tyr Lys
    130                 135                 140

Thr Val Trp Ala Ala Met Glu Glu Cys Gln Thr Leu Gly Phe Thr Arg
145                 150                 155                 160

Ala Ile Gly Val Ser Asn Phe Ser Cys Lys Lys Leu Gln Glu Leu Met
                165                 170                 175

Ala Ala Ala Lys Ile Pro Pro Val Val Asn Gln Val Glu Met Ser Pro
            180                 185                 190

Thr Leu His Gln Lys Asn Leu Arg Glu Tyr Cys Lys Ala Asn Asn Ile
        195                 200                 205

Met Ile Thr Ala His Ser Val Leu Gly Ala Ile Gly Ala Pro Trp Gly
    210                 215                 220

Ser Asn Ala Val Met Asp Ser Lys Val Leu His Gln Ile Ala Val Ala
225                 230                 235                 240

Arg Gly Lys Ser Val Ala Gln Val Ser Met Arg Trp Val Tyr Gln Gln
                245                 250                 255

Gly Ala Ser Leu Val Val Lys Ser Phe Asn Glu Gly Arg Met Lys Glu
            260                 265                 270

Asn Leu Lys Ile Phe Asp Trp Glu Leu Thr Ala Glu Asp Met Glu Lys
        275                 280                 285

Ile Ser Glu Ile Pro Gln Ser Arg Thr Ser Ser Ala Asp Phe Leu Leu
    290                 295                 300

Ser Pro Thr Gly Pro Phe Lys Thr Glu Glu Glu Phe Trp Asp Glu Lys
305                 310                 315                 320

Asp

<210> SEQ ID NO 12
<211> LENGTH: 321
<212> TYPE: PRT
<213> ORGANISM: Papaver somniferum
```

```
<220> FEATURE:
<221> NAME/KEY: MISC_FEATURE
<223> OTHER INFORMATION: COR1.5

<400> SEQUENCE: 12
```

| | | | | | | | | | | | | | | |
|---|---|---|---|---|---|---|---|---|---|---|---|---|---|---|
| Met | Glu | Ser | Asn | Gly | Val | Pro | Met | Ile | Thr | Leu | Ser | Ser | Gly | Ile | Arg |
| 1 | | | | 5 | | | | | 10 | | | | | 15 | |
| Met | Pro | Ala | Leu | Gly | Met | Gly | Thr | Val | Glu | Thr | Met | Glu | Lys | Gly | Thr |
| | | | 20 | | | | | 25 | | | | | 30 | | |
| Glu | Arg | Glu | Lys | Leu | Ala | Phe | Leu | Lys | Ala | Ile | Glu | Val | Gly | Tyr | Arg |
| | | 35 | | | | | 40 | | | | | 45 | | | |
| His | Phe | Asp | Thr | Ala | Ala | Ala | Tyr | Gln | Thr | Glu | Glu | Cys | Leu | Gly | Glu |
| | 50 | | | | | 55 | | | | | 60 | | | | |
| Ala | Ile | Ala | Glu | Ala | Leu | Gln | Leu | Gly | Leu | Ile | Lys | Ser | Arg | Asp | Glu |
| 65 | | | | | 70 | | | | | 75 | | | | | 80 |
| Leu | Phe | Ile | Thr | Ser | Lys | Leu | Trp | Cys | Ala | Asp | Ala | His | Ala | Asp | Leu |
| | | | | 85 | | | | | 90 | | | | | 95 | |
| Val | Leu | Pro | Ala | Leu | Gln | Asn | Ser | Leu | Arg | Asn | Leu | Lys | Leu | Asp | Tyr |
| | | | 100 | | | | | 105 | | | | | 110 | | |
| Leu | Asp | Leu | Tyr | Leu | Ile | His | His | Pro | Val | Ser | Leu | Lys | Pro | Gly | Lys |
| | | | 115 | | | | | 120 | | | | | 125 | | |
| Phe | Val | Asn | Glu | Ile | Pro | Lys | Asp | His | Ile | Leu | Pro | Met | Asp | Tyr | Lys |
| | 130 | | | | | 135 | | | | | 140 | | | | |
| Ser | Val | Trp | Ala | Ala | Met | Glu | Glu | Cys | Gln | Thr | Leu | Gly | Phe | Thr | Arg |
| 145 | | | | | 150 | | | | | 155 | | | | | 160 |
| Ala | Ile | Gly | Val | Cys | Asn | Phe | Ser | Cys | Lys | Lys | Leu | Gln | Glu | Leu | Met |
| | | | | 165 | | | | | 170 | | | | | 175 | |
| Ala | Thr | Ala | Asn | Ser | Pro | Pro | Val | Val | Asn | Gln | Val | Glu | Met | Ser | Pro |
| | | | 180 | | | | | 185 | | | | | 190 | | |
| Thr | Leu | His | Gln | Lys | Asn | Leu | Arg | Glu | Tyr | Cys | Lys | Ala | Asn | Asn | Ile |
| | | | 195 | | | | | 200 | | | | | 205 | | |
| Met | Ile | Thr | Ala | His | Ser | Val | Leu | Gly | Ala | Val | Gly | Ala | Ala | Trp | Gly |
| | 210 | | | | | 215 | | | | | 220 | | | | |
| Thr | Lys | Ala | Val | Met | His | Ser | Lys | Val | Leu | His | Gln | Ile | Ala | Val | Ala |
| 225 | | | | | 230 | | | | | 235 | | | | | 240 |
| Arg | Gly | Lys | Ser | Val | Ala | Gln | Val | Ser | Met | Arg | Trp | Val | Tyr | Gln | Gln |
| | | | | 245 | | | | | 250 | | | | | 255 | |
| Gly | Ala | Ser | Leu | Val | Val | Lys | Ser | Phe | Asn | Glu | Ala | Arg | Met | Lys | Glu |
| | | | 260 | | | | | 265 | | | | | 270 | | |
| Asn | Leu | Lys | Ile | Phe | Asp | Trp | Glu | Leu | Thr | Ala | Glu | Asp | Met | Glu | Lys |
| | | | 275 | | | | | 280 | | | | | 285 | | |
| Ile | Ser | Glu | Ile | Pro | Gln | Ser | Arg | Thr | Ser | Ser | Ala | Ala | Phe | Leu | Leu |
| | 290 | | | | | 295 | | | | | 300 | | | | |
| Ser | Pro | Thr | Gly | Pro | Phe | Lys | Thr | Glu | Glu | Glu | Phe | Trp | Asp | Glu | Lys |
| 305 | | | | | 310 | | | | | 315 | | | | | 320 |
| Asp | | | | | | | | | | | | | | | |

```
<210> SEQ ID NO 13
<211> LENGTH: 1340
<212> TYPE: DNA
<213> ORGANISM: Papaver rhoeas
<220> FEATURE:
<221> NAME/KEY: misc_feature
<223> OTHER INFORMATION: COR1
```

<400> SEQUENCE: 13

```
atggagagta atggtgtacc aatggttact ctaagctcgg gcattctgat gcctgcttta      60
ggtatgggaa cagctgaaac catggaaaaa ggaactgata gagagagatt ggcttttttg     120
aaagcgatag aggtcggtta cagacacttc gatacagctg ctgcatacca aagtgaagag     180
tgtcttggtg aagctatagc tgaagcacct caacttggtt taataaaatc tcgacatgaa     240
ctcttcatca cttccaagct ctggtgcact gatgctcacg ctgatcttgt cctcccctgct    300
cttcagaatt ctctgaggta aaatatttt ggtgcaaaaa ttgaacctga agcttatctg      360
catagtctgg actgtaaaac atactatatt ttgaaaactc aaactcattg tatctaacta     420
tgtttgtctt gtgtcctata ggaatcttaa attggagtat cttgatctat atttgataca     480
ctttccgcta agcctgaaac cagggaagat tgttaacgat ataccaaagg atcaaatgct     540
tccaatggac tacaaatctg tatgggcagc catggaagag tgtcgaaccc ttggattaac     600
caaggcaatc ggtgtcagca atttctcatg caaaaagctt caagagttga tggcgacagc     660
caaaagccct ccagttgtaa atgaagtgag tacaaagtag tccttacttc aacgttttga     720
taaaaaataa tggccttatt agaccttgtg gatacatgac gctattagaa tttctaccat     780
gttataaact tataacccat cttttgcatta gaactcatat aatgttgatt gctatatgat    840
taaggtggag atgagcccta ctttacaaca aaaaaatctg agagaatatt gcaaggccaa     900
taatatcatg atcacggcgt actcggtttt gggagccaga ggaaccgggt gggccagcaa     960
tgcagttatg gattctaagg tgcttcacca gattgctgcg gccagaggaa aatctgttgc    1020
tcaggttggt tgaattaatt cagcccttgt ttaacatgta taatgaatga acttcctagt    1080
ttaactaata tttgggttat atttcgtctt ttcaggttag tatgagatgg gtttaccagc    1140
aaggtgcgag tcttgtggta aaaagttaca atgaagagag gatgaaggaa aaccttaaca    1200
tattcgattg ggaattaacg gaagaagaca tggataagat cagtaacatt ccgcaatcca    1260
gagcactatc tgctgatttc ttgttatcac cgaccggacc tttcaaaact gaagaagagt    1320
tctgggatga aaggattga                                                 1340
```

<210> SEQ ID NO 14
<211> LENGTH: 321
<212> TYPE: PRT
<213> ORGANISM: Papaver rhoeas
<220> FEATURE:
<221> NAME/KEY: MISC_FEATURE
<223> OTHER INFORMATION: COR1

<400> SEQUENCE: 14

```
Met Glu Ser Asn Gly Val Pro Met Val Thr Leu Ser Ser Gly Ile Leu
1               5                   10                  15

Met Pro Ala Leu Gly Met Gly Thr Ala Glu Thr Met Glu Lys Gly Thr
            20                  25                  30

Asp Arg Glu Arg Leu Ala Phe Leu Lys Ala Ile Glu Val Gly Tyr Arg
        35                  40                  45

His Phe Asp Thr Ala Ala Ala Tyr Gln Ser Glu Glu Cys Leu Gly Glu
    50                  55                  60

Ala Ile Ala Glu Ala Pro Gln Leu Gly Leu Ile Lys Ser Arg His Glu
65                  70                  75                  80

Leu Phe Ile Thr Ser Lys Leu Trp Cys Thr Asp Ala His Ala Asp Leu
                85                  90                  95

Val Leu Pro Ala Leu Gln Asn Ser Leu Arg Asn Leu Lys Leu Glu Tyr
            100                 105                 110
```

```
Leu Asp Leu Tyr Leu Ile His Phe Pro Leu Ser Leu Lys Pro Gly Lys
            115                 120                 125

Ile Val Asn Asp Ile Pro Lys Asp Gln Met Leu Pro Met Asp Tyr Lys
        130                 135                 140

Ser Val Trp Ala Ala Met Glu Glu Cys Arg Thr Leu Gly Leu Thr Lys
145                 150                 155                 160

Ala Ile Gly Val Ser Asn Phe Ser Cys Lys Lys Leu Gln Glu Leu Met
                165                 170                 175

Ala Thr Ala Lys Ser Pro Pro Val Val Asn Glu Val Glu Met Ser Pro
            180                 185                 190

Thr Leu Gln Gln Lys Asn Leu Arg Glu Tyr Cys Lys Ala Asn Asn Ile
        195                 200                 205

Met Ile Thr Ala Tyr Ser Val Leu Gly Ala Arg Gly Thr Gly Trp Ala
210                 215                 220

Ser Asn Ala Val Met Asp Ser Lys Val Leu His Gln Ile Ala Ala Ala
225                 230                 235                 240

Arg Gly Lys Ser Val Ala Gln Val Ser Met Arg Trp Val Tyr Gln Gln
                245                 250                 255

Gly Ala Ser Leu Val Val Lys Ser Tyr Asn Glu Glu Arg Met Lys Glu
            260                 265                 270

Asn Leu Asn Ile Phe Asp Trp Glu Leu Thr Glu Glu Asp Met Asp Lys
        275                 280                 285

Ile Ser Asn Ile Pro Gln Ser Arg Ala Leu Ser Ala Asp Phe Leu Leu
    290                 295                 300

Ser Pro Thr Gly Pro Phe Lys Thr Glu Glu Glu Phe Trp Asp Glu Lys
305                 310                 315                 320

Asp

<210> SEQ ID NO 15
<211> LENGTH: 1613
<212> TYPE: DNA
<213> ORGANISM: Papaver orientale
<220> FEATURE:
<221> NAME/KEY: misc_feature
<223> OTHER INFORMATION: COR1

<400> SEQUENCE: 15
atggagagta atggtgtacc tatgatcact ctcagctccg gcattcggat gcctgcttta        60
ggtatgggaa cagctgaaaa atggttaaa ggaacagaaa gagagaaatt ggcgttttg        120 aaagcgatag aggtcggtta cagacgcttc gatacagctg ctgcatacca aactgaagag       180
tgtcttggtg aagctatagc tgaagcactt caacttggtc taataaaatc tcgagatgaa       240
ctcttcatca cttccaagct ctggtgcact gatgctcacg ttgatcttgt cctcccctgct    300 cttcagaggt aaaaatattt ttgtgaaaaa attgaaccta tcataggcac acaacggtt       360 cttaaacatc tatatataga acttcagaat attcaaattg atattaattc atcttgtttt       420
gtgtcatata ggaatctcaa attggagtat cttgatctat atttgataca ctttccgata       480
agcttgaagc cagggaagat tgtcaacgat ataccgaagg atcaaatgct ccaatggac       540 tccaaatctg tatgggcagc catggaaggg tgtcaggccc ttgggttcac tagggcaatc      600
ggtgtcagta attttttcatg caaaaagctt caagagttga tggcgacagc aacagccct      660 ccagttgtaa atgaagtgag tacaaattag ttcttaattc ttactgcaac gtgtggataa      720
aaattagtgg ttgccttgtt cggccttggc gccatttgtt ggaatgttat aaatgcccac     780 catttttagtt gacgttacgc aaatatccc gaagtaaaa ataatatttt ttggagtcga     840
```

```
tttaagacgg ttgtttttat ttttggagac aacttgagat tgttgcttcc acttttagag    900
tctaacttgc ataaagttgg gtccgttcta ggaacaactt gagatggttg ctttcacttt    960
tagaaggtat gggtatttgt gaatgttgaa taagggcata ttccaagagt tagattttaa   1020
aggtatttaa ataagtttcc cataaattac caccatttga caagcattta gcccatgttc   1080
gcattagaaa tcttacaatg ttattgctta cgatcaaggt ggagatgagc ccgatttccc   1140
aacaaaaaaa tttgagagca tattgcaagg ccaataatat catgatcact gcatactcgg   1200
ttttgggatc cagaggagcc gcatggggca gcaatgcagt tatggattct aaggtgcttc   1260
accagattgc tgtggccata ggaaaatctg ttgctcaggt tggttgaatt ctccccttg    1320 taatcacatg tataatgaac ttcgtagttt taactaatat ttatgttata tatatttcgt   1380
ctgttcaggt tagcatgaga tgggtttacc agcaaggtgc gtgtcttgtg gtgaaaagtt   1440
tcaatgaagg gaggatgaag gaaaaccttaa aatattcga ttgggaacta acggaagaag   1500
acatgtataa gatcagtgag attccgcaat ccagaacagt ctctgctgat ttcttgttat   1560
caccgactgg accttttcaaa actgaagaag agttctggga tgagaaggat tga         1613
```

<210> SEQ ID NO 16
<211> LENGTH: 318
<212> TYPE: PRT
<213> ORGANISM: Papaver orientale
<220> FEATURE:
<221> NAME/KEY: MISC_FEATURE
<223> OTHER INFORMATION: COR1

<400> SEQUENCE: 16

```
Met Glu Ser Asn Gly Val Pro Met Ile Thr Leu Ser Ser Gly Ile Arg
1               5                   10                  15

Met Pro Ala Leu Gly Met Gly Thr Ala Glu Lys Met Val Lys Gly Thr
            20                  25                  30

Glu Arg Glu Lys Leu Ala Phe Leu Lys Ala Ile Glu Val Gly Tyr Arg
        35                  40                  45

Arg Phe Asp Thr Ala Ala Ala Tyr Gln Thr Glu Glu Cys Leu Gly Glu
    50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Thr Asp Ala His Val Asp Leu
                85                  90                  95

Val Leu Pro Ala Leu Gln Arg Asn Leu Lys Leu Glu Tyr Leu Asp Leu
            100                 105                 110

Tyr Leu Ile His Phe Pro Ile Ser Leu Lys Pro Gly Lys Ile Val Asn
        115                 120                 125

Asp Ile Pro Lys Asp Gln Met Leu Pro Met Asp Ser Lys Ser Val Trp
    130                 135                 140

Ala Ala Met Glu Gly Cys Gln Ala Leu Gly Phe Thr Arg Ala Ile Gly
145                 150                 155                 160

Val Ser Asn Phe Ser Cys Lys Lys Leu Gln Glu Leu Met Ala Thr Ala
                165                 170                 175

Asn Ser Pro Pro Val Val Asn Glu Val Glu Met Ser Pro Ile Phe Gln
            180                 185                 190

Gln Lys Asn Leu Arg Ala Tyr Cys Lys Ala Asn Asn Ile Met Ile Thr
        195                 200                 205

Ala Tyr Ser Val Leu Gly Ser Arg Gly Ala Ala Trp Gly Ser Asn Ala
    210                 215                 220
```

```
Val Met Asp Ser Lys Val Leu His Gln Ile Ala Ala Ile Gly Lys
225                 230                 235                 240

Ser Val Ala Gln Val Ser Met Arg Trp Val Tyr Gln Gln Gly Ala Cys
                245                 250                 255

Leu Val Val Lys Ser Phe Asn Glu Gly Arg Met Lys Glu Asn Leu Lys
                260                 265                 270

Ile Phe Asp Trp Glu Leu Thr Glu Glu Asp Met Tyr Lys Ile Ser Glu
            275                 280                 285

Ile Pro Gln Ser Arg Thr Val Ser Ala Asp Phe Leu Leu Ser Pro Thr
        290                 295                 300

Gly Pro Phe Lys Thr Glu Glu Glu Phe Trp Asp Glu Lys Asp
305                 310                 315
```

<210> SEQ ID NO 17
<211> LENGTH: 1347
<212> TYPE: DNA
<213> ORGANISM: Papaver nudicaule
<220> FEATURE:
<221> NAME/KEY: misc_feature
<223> OTHER INFORMATION: COR1

<400> SEQUENCE: 17

```
atggagagta atggtgtacc tgtgataact ctcagctcgg gcattgggat gcctgtttta      60
ggcatgggaa cagctgaaaa acttattaaa ggatctgaaa gagagaagtt ggcgttttg     120
aaggcgatgg agctgggtta cagacacttc gacacagctg ctatttacca aactgaagag     180
tctcttggtg aagctatagc tgaagcactt caaattggcc taatcgaaac tcgagatgaa     240
ctcttcgtca cttccaagct ctggtgcgtt gatgctcacc tgatcttgt cctccccgct      300
cttcggaatt ccctcaggta agaaatttgg tgcaaattga accaaaggct tatgtgcata     360
gttactgtat ctggagttct taaactttat ctaattctga acattcaaa ttgattgaca      420
aggaatgcga acctcaacta gtcatcctgt tttgtgcaat ataggaatct taaattggag     480
tatcttgatt tatatctgat acactatccg gcaagactca agccagggga gattgttgtc     540
gatgtgccag gtatgaaat acttccgatg gactacaggt ctgtatgggc agcgatggaa      600
gagtgtcaga accttggctt cactaagtct attggtgtca gcattttttc gtgcaaaaag     660
attcaagagt tgatggcgac agccaacatc cctccagttg taaatcaagt aagtatcaaa     720
aaattagtgg tttccttatt cgaccttgaa gagacttatt gcaaatgaaa ttcccaccat     780
ttgacaagca tacccaac attcacataa aattctactc ttatatgatt aaggtggaga      840
tgagcccgac attccaacaa aaatatctga gaatattg caaggctaat aatatcatga       900
tcagtgcata ctcgatcttg ggatcgaaag gaacattttg gggatccaat gcaatcatgg     960
gttctgatgt gcttcaccag attgctgtgg ccagaggaaa atctattgct caggttggtc    1020
aaatttcccg ctttgcatca catgcatctc cttatactaa tgtctaatta ataacatttt    1080
cttaatttaa catacatttc ttattatatt tcatctgttc aggttagtat gaggtgggtt    1140
tacgagcaag gtgtgtttct tatagtgaaa agttttaatg aagagaggat gagggaaaac    1200
ttaaagatat tcgattggga actgactcca gacgacttgg aaaagatcgg tgagattcct    1260
caatgcagaa cagtgagtgg agatttttg atatcagcta gcggaccttt caaatcctta    1320
gaagagctct gggatgagaa ggattga                                       1347
```

<210> SEQ ID NO 18
<211> LENGTH: 321
<212> TYPE: PRT
<213> ORGANISM: Papaver nudicaule
<220> FEATURE:
<221> NAME/KEY: MISC_FEATURE
<223> OTHER INFORMATION: COR1

<400> SEQUENCE: 18

```
Met Glu Ser Asn Gly Val Pro Val Ile Thr Leu Ser Ser Gly Ile Gly
1               5                   10                  15

Met Pro Val Leu Gly Met Gly Thr Ala Glu Lys Leu Ile Lys Gly Ser
            20                  25                  30

Glu Arg Glu Lys Leu Ala Phe Leu Lys Ala Met Glu Leu Gly Tyr Arg
        35                  40                  45

His Phe Asp Thr Ala Ala Ile Tyr Gln Thr Glu Glu Ser Leu Gly Glu
    50                  55                  60

Ala Ile Ala Glu Ala Leu Gln Ile Gly Leu Ile Glu Thr Arg Asp Glu
65                  70                  75                  80

Leu Phe Val Thr Ser Lys Leu Trp Cys Val Asp Ala His Pro Asp Leu
                85                  90                  95

Val Leu Pro Ala Leu Arg Asn Ser Leu Arg Asn Leu Lys Leu Glu Tyr
            100                 105                 110

Leu Asp Leu Tyr Leu Ile His Tyr Pro Ala Arg Leu Lys Pro Gly Glu
        115                 120                 125

Ile Val Val Asp Val Pro Gly Tyr Glu Ile Leu Pro Met Asp Tyr Arg
130                 135                 140

Ser Val Trp Ala Ala Met Glu Glu Cys Gln Asn Leu Gly Phe Thr Lys
145                 150                 155                 160

Ser Ile Gly Val Ser Asn Phe Ser Cys Lys Lys Ile Gln Glu Leu Met
                165                 170                 175

Ala Thr Ala Asn Ile Pro Pro Val Val Asn Gln Val Glu Met Ser Pro
            180                 185                 190

Thr Phe Gln Gln Lys Tyr Leu Arg Glu Tyr Cys Lys Ala Asn Asn Ile
        195                 200                 205

Met Ile Ser Ala Tyr Ser Ile Leu Gly Ser Lys Gly Thr Phe Trp Gly
210                 215                 220

Ser Asn Ala Ile Met Gly Ser Asp Val Leu His Gln Ile Ala Val Ala
225                 230                 235                 240

Arg Gly Lys Ser Ile Ala Gln Val Ser Met Arg Trp Val Tyr Glu Gln
                245                 250                 255

Gly Val Phe Leu Ile Val Lys Ser Phe Asn Glu Glu Arg Met Arg Glu
            260                 265                 270

Asn Leu Lys Ile Phe Asp Trp Glu Leu Thr Pro Asp Asp Leu Glu Lys
        275                 280                 285

Ile Gly Glu Ile Pro Gln Cys Arg Thr Val Ser Gly Asp Phe Leu Ile
290                 295                 300

Ser Ala Ser Gly Pro Phe Lys Ser Leu Glu Glu Leu Trp Asp Glu Lys
305                 310                 315                 320

Asp
```

<210> SEQ ID NO 19
<211> LENGTH: 1632
<212> TYPE: DNA
<213> ORGANISM: Papaver bracteatum
<220> FEATURE:
<221> NAME/KEY: misc_feature
<223> OTHER INFORMATION: COR1

<400> SEQUENCE: 19

| | |
|---|---:|
| atggagagta atggtgtacc tatgatcact ctcagttccg gcattcggat gcctgcttta | 60 |
| ggtatgggaa cagttgaaac aatggaaaaa ggaacagaaa gagagaaatt ggcgttttg | 120 |
| aaagcgatag aggtcggtta cagacatttc gatacagctg ctgcatacca aactgaagag | 180 |
| tgtcttggtg aagctatagc tgaagcactt caactcggtc taataaaatc tcgagaggaa | 240 |
| ctcttcatca cttccaagct ctggtgcact gatgctcacg ctgatcttgt cctccctgct | 300 |
| cttcagaatt ctctgaggta aaaatatttt tgtgcaaaaa ttgaacccaa ggctgatgta | 360 |
| cataggcatg caccacaaca gttcttaaac atctatatat agaacttcag aatattcaaa | 420 |
| ttgatattaa ttcatcttgt tttttgtcat aaaggaatct caaattggag tatcttgatc | 480 |
| tatatttgat acactttccg gtaagcttga agccagggaa gattgttagc gatataccaa | 540 |
| aggatcaaat gcttccaatg gactacaaat ctgtatgggt agccatggaa gagtgtcaga | 600 |
| cccttggctt cactagggca atcggtgtca gtaattttc atgcaaaaag cttcaagagt | 660 |
| tgatggcgac agccaacagc cctccagttg taatgaagt gagtacaaat tagtccttaa | 720 |
| ttcttacttc aatgtgtgga taaaaattag tggttgcctt gttcgacctt gacgccattt | 780 |
| gttggaatgt tataaatgcc ctccatttta gttgaccttg cacaaatatc cccgaggtaa | 840 |
| aaaataatat ttttggagt ctgacttaag acggtttgtt tttacttttc gagacaactt | 900 |
| gagatggttg tttccacttt tagagtcaac ttgtataaag ttgggtccgt tctgggaaca | 960 |
| acttgtgcta gttgcttcca cttttagaag gtatgtgtat ttttaaactt tgaataaggg | 1020 |
| catattccaa gagttagatt ttaaagggta tttaaataag tttcccataa attaccacca | 1080 |
| tttgaccagc atttagccca tgttcgcatt agaaatctta caatgttatt gcttatgatt | 1140 |
| aaggtgggaga tgagcccggt tttccaacaa aaaaatttga gagcatattg caaggccaat | 1200 |
| aatatcatga tcactgcata ctcggttttg ggagccagag gagccgcatg gggcagcaat | 1260 |
| gcagttatgg attctaaggt gcttcacgag attgctgtgg ccagaggaaa atctgctgcc | 1320 |
| caggttggtt gaattctcct cttccaatca catgtataat ggacttctta gtttaactta | 1380 |
| tatttgtgtt atatttcgtc tgttcaggtt agtatgagat gggtttacca gcaaggcgcg | 1440 |
| tgtcttgtgg tgaaaagttt caatgaagag aggatgaagg aaaaccttaa gatattcgat | 1500 |
| tgggaactat cagcagaaga catggaaaag atcagtgaaa ttccgcaatg tagaacaagc | 1560 |
| tctgctgatt tcttgttatc accgactggg cctttcaaaa ctgaagaaga gttctgggat | 1620 |
| gagaaggatt ga | 1632 |

<210> SEQ ID NO 20
<211> LENGTH: 321
<212> TYPE: PRT
<213> ORGANISM: Papaver bracteatum
<220> FEATURE:
<221> NAME/KEY: MISC_FEATURE
<223> OTHER INFORMATION: COR1

<400> SEQUENCE: 20

Met Glu Ser Asn Gly Val Pro Met Ile Thr Leu Ser Ser Gly Ile Arg
1               5                   10                  15

Met Pro Ala Leu Gly Met Gly Thr Val Glu Thr Met Glu Lys Gly Thr
            20                  25                  30

```
Glu Arg Glu Lys Leu Ala Phe Leu Lys Ala Ile Glu Val Gly Tyr Arg
             35                  40                  45

His Phe Asp Thr Ala Ala Ala Tyr Gln Thr Glu Cys Leu Gly Glu
 50                  55                  60

Ala Ile Ala Glu Ala Leu Gln Leu Gly Leu Ile Lys Ser Arg Glu Glu
 65                  70                  75                  80

Leu Phe Ile Thr Ser Lys Leu Trp Cys Thr Asp Ala His Ala Asp Leu
                 85                  90                  95

Val Leu Pro Ala Leu Gln Asn Ser Leu Arg Asn Leu Lys Leu Glu Tyr
            100                 105                 110

Leu Asp Leu Tyr Leu Ile His Phe Pro Val Ser Leu Lys Pro Gly Lys
            115                 120                 125

Ile Val Ser Asp Ile Pro Lys Asp Gln Met Leu Pro Met Asp Tyr Lys
            130                 135                 140

Ser Val Trp Val Ala Met Glu Glu Cys Gln Thr Leu Gly Phe Thr Arg
145                 150                 155                 160

Ala Ile Gly Val Ser Asn Phe Ser Cys Lys Lys Leu Gln Glu Leu Met
                165                 170                 175

Ala Thr Ala Asn Ser Pro Pro Val Val Asn Glu Val Glu Met Ser Pro
            180                 185                 190

Val Phe Gln Gln Lys Asn Leu Arg Ala Tyr Cys Lys Ala Asn Asn Ile
            195                 200                 205

Met Ile Thr Ala Tyr Ser Val Leu Gly Ala Arg Gly Ala Ala Trp Gly
            210                 215                 220

Ser Asn Ala Val Met Asp Ser Lys Val Leu His Glu Ile Ala Val Ala
225                 230                 235                 240

Arg Gly Lys Ser Ala Ala Gln Val Ser Met Arg Trp Val Tyr Gln Gln
                245                 250                 255

Gly Ala Cys Leu Val Val Lys Ser Phe Asn Glu Glu Arg Met Lys Glu
            260                 265                 270

Asn Leu Lys Ile Phe Asp Trp Glu Leu Ser Ala Glu Asp Met Glu Lys
            275                 280                 285

Ile Ser Glu Ile Pro Gln Cys Arg Thr Ser Ser Ala Asp Phe Leu Leu
            290                 295                 300

Ser Pro Thr Gly Pro Phe Lys Thr Glu Glu Glu Phe Trp Asp Glu Lys
305                 310                 315                 320

Asp

<210> SEQ ID NO 21
<211> LENGTH: 1386
<212> TYPE: DNA
<213> ORGANISM: Papaver somniferum

<400> SEQUENCE: 21
gttcttaatt cattaattaa tttagaaaaa tcatggagaa agcaaaactt atgaagctag      60
gtaatggtat ggaaatacca agtgttcaag aattggctaa actcacgctt gccgaaattc     120
catctcgata cgtatgcgcc aatgaaaacc ttttgttgcc tatgggtgca tctgtcataa     180
atgatcatga aaccattcct gtcatcgata tagaaaattt attatctcca gaaccaataa     240
tcggaaagtt agaattagat aggcttcatt ttgcttgcaa agaatggggt ttttttcagg     300
tagtgaacca tggagtcgac gcttcattgg tggatagtgt aaaatcagaa attcaaggtt     360
tctttaacct ttctatggat gagaaaacta aatatgaaca ggaagatgga gatgtggaag     420
gatttggaca aggctttatt gaatcagagg accaaacact tgattgggca gatatattta     480
```

```
tgatgttcac tcttccactc catttaagga agcctcactt attttcaaaa ctcccagtgc      540
ctctcaggga gacaatcgaa tcctactcat cagaaatgaa aaagttatcc atggttctct      600
ttaataagat ggaaaaagct ctacaagtac aagcagccga gattaagggt atgtcagagg      660
tgtttataga tgggacacaa gcaatgagga tgaactatta tccccttgt cctcaaccaa       720 atctcgccat cggtcttacg tcgcactcgg attttggcgg tttgacaatc ctccttcaaa      780
tcaacgaagt ggaaggatta cagataaaaa gagaggggac atggatttca gtcaaacctc      840
tacctaatgc gttcgtagtg aatgttggag atattttgga gataatgact aatggaattt      900
accatagtgt cgatcaccgg gcagtagtaa actcaacaaa tgagaggctc tcaatcgcaa      960
catttcatga ccctagtcta gagtcggtaa taggcccaat atcaagcttg attactccag     1020
agacacctgc tttgtttaaa agtggatcta catatgggga tcttgtggag gaatgtaaaa     1080
caaggaagct cgatggaaaa tcatttcttg actccatgag gatttgaaaa ctcaagaaaa     1140
aataatacga cgtgattgca tgtcagattc aactatcctt ttgtcgtttt ttggtgctcg     1200
agtccttaat tgttttgatc attgcttttg attctaatta ataagactt tctcaagaac      1260 cacatgtaat gtacctttac tttcagaaaa taaaaagtat tgaggcacaa atgagaaaat     1320
tgagagagtg cttgagaagt gtaatttctc gaaagtgcgt tgtgtttgaa aaaaaaaaa     1380 aaaaaa                                                               1386
```

<210> SEQ ID NO 22
<211> LENGTH: 364
<212> TYPE: PRT
<213> ORGANISM: Papaver somniferum

<400> SEQUENCE: 22

```
Met Glu Lys Ala Lys Leu Met Lys Leu Gly Asn Gly Met Glu Ile Pro
1               5                   10                  15

Ser Val Gln Glu Leu Ala Lys Leu Thr Leu Ala Glu Ile Pro Ser Arg
            20                  25                  30

Tyr Val Cys Ala Asn Glu Asn Leu Leu Leu Pro Met Gly Ala Ser Val
        35                  40                  45

Ile Asn Asp His Glu Thr Ile Pro Val Ile Asp Ile Glu Asn Leu Leu
    50                  55                  60

Ser Pro Glu Pro Ile Ile Gly Lys Leu Glu Leu Asp Arg Leu His Phe
65                  70                  75                  80

Ala Cys Lys Glu Trp Gly Phe Phe Gln Val Val Asn His Gly Val Asp
                85                  90                  95

Ala Ser Leu Val Asp Ser Val Lys Ser Glu Ile Gln Gly Phe Phe Asn
            100                 105                 110

Leu Ser Met Asp Glu Lys Thr Lys Tyr Glu Gln Glu Asp Gly Asp Val
        115                 120                 125

Glu Gly Phe Gly Gln Gly Phe Ile Glu Ser Gly Asp Gln Thr Leu Asp
    130                 135                 140

Trp Ala Asp Ile Phe Met Met Phe Thr Leu Pro Leu His Leu Arg Lys
145                 150                 155                 160

Pro His Leu Phe Ser Lys Leu Pro Val Pro Leu Arg Glu Thr Ile Glu
                165                 170                 175

Ser Tyr Ser Ser Glu Met Lys Lys Leu Ser Met Val Leu Phe Asn Lys
            180                 185                 190

Met Glu Lys Ala Leu Gln Val Gln Ala Ala Glu Ile Lys Gly Met Ser
        195                 200                 205
```

```
Glu Val Phe Ile Asp Gly Thr Gln Ala Met Arg Met Asn Tyr Tyr Pro
    210             215                 220

Pro Cys Pro Gln Pro Asn Leu Ala Ile Gly Leu Thr Ser His Ser Asp
225             230                 235                 240

Phe Gly Gly Leu Thr Ile Leu Leu Gln Ile Asn Glu Val Glu Gly Leu
                245                 250                 255

Gln Ile Lys Arg Glu Gly Thr Trp Ile Ser Val Lys Pro Leu Pro Asn
            260             265                 270

Ala Phe Val Asn Val Gly Asp Ile Leu Glu Ile Met Thr Asn Gly
        275             280                 285

Ile Tyr His Ser Val Asp His Arg Ala Val Val Asn Ser Thr Asn Glu
    290             295                 300

Arg Leu Ser Ile Ala Thr Phe His Asp Pro Ser Leu Glu Ser Val Ile
305             310                 315                 320

Gly Pro Ile Ser Ser Leu Ile Thr Pro Glu Thr Pro Ala Leu Phe Lys
                325             330                 335

Ser Gly Ser Thr Tyr Gly Asp Leu Val Glu Glu Cys Lys Thr Arg Lys
            340             345                 350

Leu Asp Gly Lys Ser Phe Leu Asp Ser Met Arg Ile
            355             360
```

COMPOSITIONS AND METHODS FOR MAKING ALKALOID MORPHINANS

RELATED APPLICATIONS

This application is a national phase entry application of Patent Cooperation Treaty Application No. PCT/CA2015/050796, which claims the benefit under 35 USC § 119(e) from U.S. Provisional Patent Application No. 62/040,754, filed on Aug. 22, 2014, both of which are incorporated by reference herein in their entirety.

INCORPORATION OF SEQUENCE LISTING

A computer readable form of the Sequence Listing "21806-P46963US01_SequenceListing.txt" (53,248 bytes), submitted via EFS-WEB and amended on Apr. 4, 2017, is herein incorporated by reference.

FIELD OF THE DISCLOSURE

The compositions and methods disclosed herein relate to a class of chemical compounds known as alkaloids and methods for making alkaloids. More particularly, the present disclosure relates to alkaloid morphinans and processes for making the same.

BACKGROUND OF THE DISCLOSURE

The following paragraphs are provided by way of background to the present disclosure. They are not however an admission that anything discussed therein is prior art or part of the knowledge of persons skilled in the art.

Alkaloids belonging to the class of chemical compounds known as morphinans (i.e. alkaloid morphinans) have long been recognized to be useful as therapeutic agents, and as precursor compounds for use in the manufacture of therapeutic agents. Neopine, for example, is produced by plants belonging to the Papaveraceae and has been isolated from opium poppy (*Papaver somniferum*) (Dobbie J. J. and Lauder, A. (1911), J. Chemical Society, 34-5). It is known that neopine in planta is produced from a precursor compound named thebaine. However it is not clear which plant genes and polypeptides are involved in catalyzing the conversion reaction(s) resulting in the production of neopine. Currently neopine may be harvested from natural sources, such as opium poppy. Alternatively, neopine may be prepared synthetically. The latter may be achieved by oxymercuration of thebaine or by reduction of or 14-bromocodeinone or 14-bromo-codeine (NaBH$_4$) which yields neopine and its isomers (Poppy, the genus *Papaver*, 1998, pp 116, Harwood Academic Publishers, Editor: Bernath, J.)

The existing manufacturing methods for neopine and related morphinans however suffer from low yields of neopine and morphinans and/or are expensive. No methods exist to biosynthetically make neopine. There exists therefore in the art a need for improved methods for the synthesis of neopine and related morphinans.

SUMMARY OF THE DISCLOSURE

The following paragraphs are intended to introduce the reader to the more detailed description that follows and not to define or limit the claimed subject matter of the present disclosure.

The present disclosure relates to certain alkaloids belonging to the class of morphinans, as well as to methods of making such morphinans. Accordingly, the present disclosure provides in at least one aspect a method of making a second morphinan having a $C_7$-$C_8$ saturated carbon bond and a $C_8$-$C_{14}$ mono-unsaturated carbon bond comprising:
  (a) providing a first morphinan having a $C_7$-$C_8$ mono-unsaturated carbon bond and a $C_8$-$C_{14}$ saturated carbon bond; and
  (b) contacting the first morphinan with a codeine isomerase or codeinone reductase capable of converting the first morphanin into the second morphinan.

In preferred embodiments, the method further comprises a step
  (c) recovering the second morphinan.

In preferred embodiments, the first morphinan and the second morphinan possess a bridging oxygen atom between carbon atoms $C_4$ and $C_5$ forming a tetrahydrofuranyl ring within the morphinan structure (furanyl-morphinan).

The present disclosure further provides, in at least one aspect, a method of making a second morphinan comprising:
  (a) providing a first morphinan;
  (b) contacting the first morphinan with a codeine isomerase or codeinone reductase capable of converting the first morphinan under conditions that permit the conversion of the first morphinan into the second morphinan;
  wherein the first morphinan has the chemical formula (I):

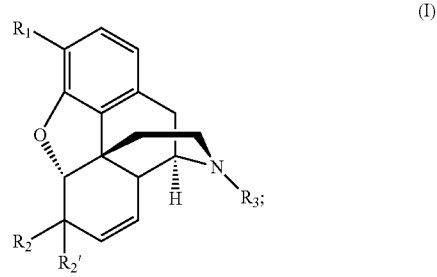

and
wherein the second morphinan has the chemical formula (II):

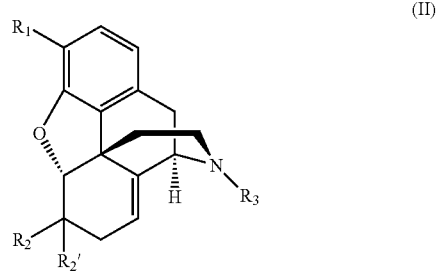

wherein, in the first and the second morphinan, $R_1$ represents a hydroxyl group or a methoxy group; wherein in the first and the second morphinan $R_2$ represents a hydroxyl group and $R_2'$ represents a hydrogen atom, or taken together, $R_2$ and $R_2'$ form an oxo group; and wherein in the first and the second morphinan $R_3$ represents a hydrogen atom, or a methyl group, wherein when $R_3$ represents a methyl group, the nitrogen atom bonded to $R_3$ is optionally in the form of an N-oxide.

In further preferred embodiments, the nitrogen atom in the morphinan is methylated (i.e. $R_3$ is a methyl group).

In further preferred embodiments, the nitrogen atom in the morphinan is hydrogenated (i.e. $R_3$ is a hydrogen).

In further preferred embodiments, the nitrogen is a methylated and N-oxidized.

In further particularly preferred embodiments, in the first and the second morphinan, $R_1$ is a methoxy group; $R_2$ is a hydroxyl group and $R_2'$ is a hydrogen atom; and $R_3$ is a methyl group, providing for the first morphinan having the chemical formula (III):

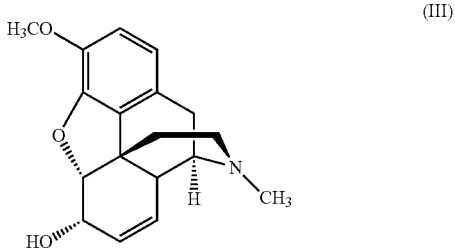

(III)

also known as codeine; and, providing for the second morphinan having the chemical formula (IV):

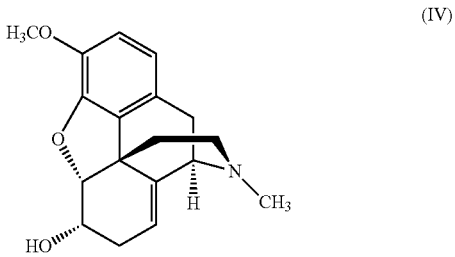

(IV)

also known as neopine.

In further preferred embodiments, the codeine isomerase or the codeinone reuctase are a codeine isomerase or codeinone reductase obtainable from or obtained from *Papaver somniferum*.

In accordance with the present disclosure, the methods may be conducted in vitro or in vivo including, but not limited to, in plants, plant cell cultures, microorganisms, and cell-free systems.

In further embodiments, provided herein is a method for preparing a morphinan having chemical formula (II) comprising:
 (a) providing a chimeric nucleic acid sequence comprising as operably linked components:
  (i) a nucleic acid sequence encoding a codeine isomerase or codeinone reductase polypeptide;
  (ii) one or more nucleic acid sequences capable of controlling expression in a host cell;
 (b) introducing the chimeric nucleic acid sequence into a host cell that endogenously produces or is exogenously supplied with a morphinan substrate;
 (c) growing the host cell to produce codeine isomerase or codeinone reductase and to produce the morphinan having chemical formula (II); and
 (d) recovering morphinan having chemical formula (II) from the cell; wherein $R_1$ represents a hydroxyl group or a methoxy group; wherein $R_2$ represents a hydroxyl group or an oxo group; and wherein $R_3$ represents a hydrogen atom, or a methyl group, wherein when $R_3$ represents a methyl group the N is optionally an N-oxide.

Provided herein is further a method for preparing a codeine isomerase, the method comprising:
 (a) providing a chimeric nucleic acid sequence comprising as operably linked components:
  (i) a nucleic acid sequence encoding a codeine isomerase or codeinone reductase; and
  (ii) one or more a nucleic acid sequences capable of controlling expression in a host cell;
 (b) introducing the chimeric nucleic acid sequence into a host cell and growing the host cell to produce the codeine isomerase or codeinone reductase; and
 (c) recovering the codeine isomerase polypeptide or codeinone reductase from the host cell.

The present disclosure, still further, provides compositions for making a morphinan, comprising a polypeptide capable of, in a first morphinan having a mono-unsaturated $C_7$-$C_8$ bond and a saturated $C_8$-$C_{14}$ bond:
 (i) saturating the $C_7$-$C_8$ bond; and
 (ii) unsaturating the $C_8$-$C_{14}$ bond, to form a second morphinan having a saturated $C_7$-$C_8$ and a mono-unsaturated $C_8$-$C_{14}$ bond.

In preferred embodiments, the polypeptide is a codeine isomerase or codeinone reductase obtainable or obtained from *Papaversomniferum*.

The present disclosure, still further, provides compositions comprising nucleic acid sequences encoding a polypeptide capable of, in a first morphinan having a mono-unsaturated $C_7$-$C_8$ bond and a saturated $C_8$-$C_{14}$ bond:
 (i) saturating the $C_7$-$C_8$ bond; and
 (ii) unsaturating the $C_8$-$C_{14}$ bond, to form a second morphinan having a saturated $C_7$-$C_8$ and a mono-unsaturated $C_8$-$C_{14}$ bond.

Other features and advantages of the present disclosure will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described in relation to its Figures. The Figures provided herein are provided for illustration purposes and are not intended to limit the present disclosure.

FIG. 6 depicts a comparison between the polynucleotide sequences of codeine isomerase (also set forth in SEQ. ID NO: 2) (sequence labeled "CDI") and codeinone reductase, used as a control as further described in Example 1 (sequence labeled "COR 1.3"). Amino acids are numbered from the N-terminus.

DETAILED DESCRIPTION OF THE DISCLOSURE

Various compositions and processes will be described below to provide an example of an embodiment of each claimed subject matter. No embodiment described below limits any claimed subject matter and any claimed subject matter may cover processes, compositions or systems that differ from those described below. The claimed subject matter is not limited to compositions or processes having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicants, inventors or owners do not intend to abandon, disclaim or dedicate to the public any such subject matter by its disclosure in this document.

All publications, patents and patent applications are herein incorporated by reference in their entirety to the same extent as if each individual publication, patent or patent application was specifically and individually indicated to be incorporated by reference in its entirety.

Definitions

Figure 1:
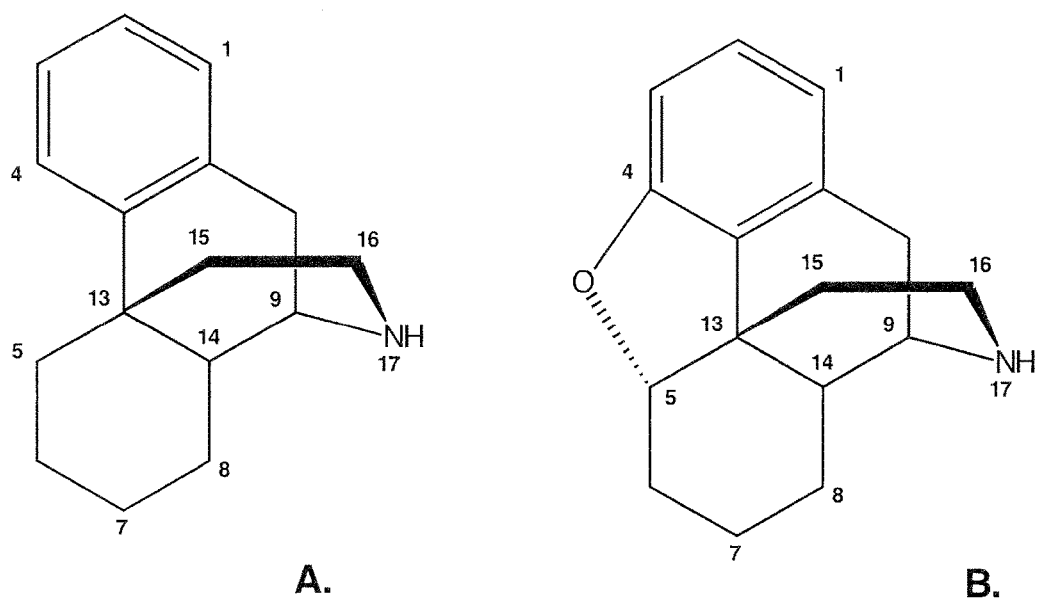
FIG. 1 depicts a prototype chemical structure of morphinan (FIG. 1A) and furanyl morphinan (FIG. 1B). Various atoms within the structures have been numbered for ease of reference.

The term "morphinan", as used herein, refers to a class of chemical compounds comprising the prototype chemical structure shown in FIG. 1A. Certain specific carbon and nitrogen atoms are referred to herein by reference to their position within the morphinan structure e.g. $C_1$, $C_2$, $N_{17}$ etc. The pertinent atom numbering is shown in FIG. 1A The term "furanyl-morphinan" as used herein refers to a class of chemical compounds comprising the prototype chemical structure shown in FIG. 1B. Furanyl-morphinans may be derived from morphinans by the formation of a tetrahydrofuranyl ring structure established by a bridging oxygen between $C_4$ and $C_5$. It is noted that the tetrahydrofuranyl group may also be referred to as a 2,3 dihydrofuranyl ring structure due to benzene resonance.

Figure 2:
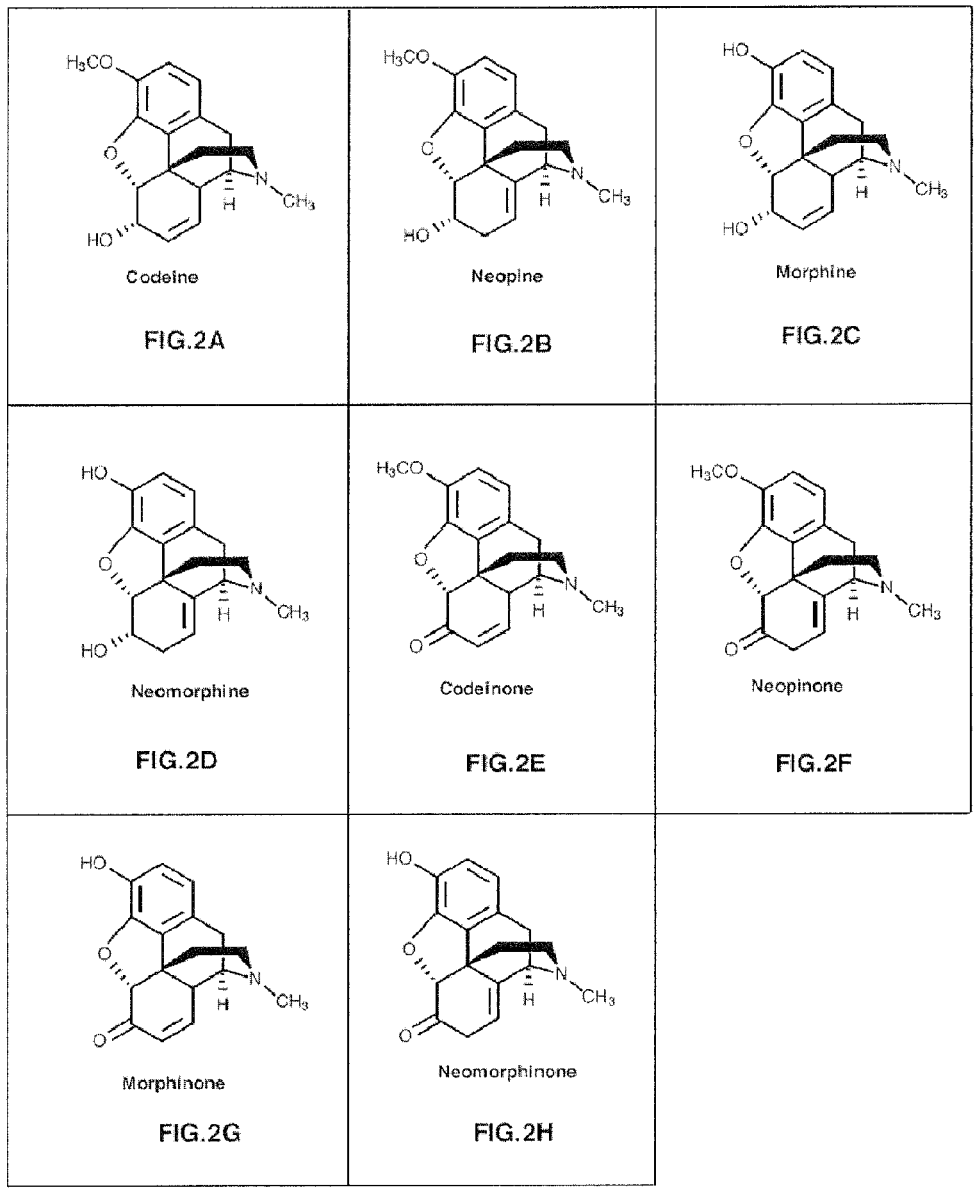
FIG. 2 depicts the chemical structures of certain morphinans, notably morphinans having a methylated $N_{17}$: codeine (FIG. 2A), neopine (FIG. 2B), morphine (FIG. 2C), neomorphine (FIG. 2D), codeinone (FIG. 2E), neopinone (FIG. 2F), morphinone (FIG. 2G), neomorphinone (FIG. 2H).

The term "codeine" as used herein refers to a chemical compound having the structure set forth in FIG. 2A, and further represented by the chemical formula (III).

The term "neopine" as used herein refers to a chemical compound having the structure set forth in FIG. 2B, and further represented by the chemical formula (IV).

The term "morphine" as used herein refers to a chemical compound having the structure set forth in FIG. 2C.

The term "neomorphine" as used herein refers to a chemical compound having the structure set forth in FIG. 2D.

The term "codeinone" as used herein refers to a chemical compound having the structure set forth in FIG. 2E.

The term "neopinone" as used herein refers to a chemical compound having the structure set forth in FIG. 2F.

The term "morphinone" as used herein refers to a chemical compound having the structure set forth in FIG. 2G.

The term "neomorphinone" as used herein refers to a chemical compound having the structure set forth in FIG. 2H.

Figure 3:
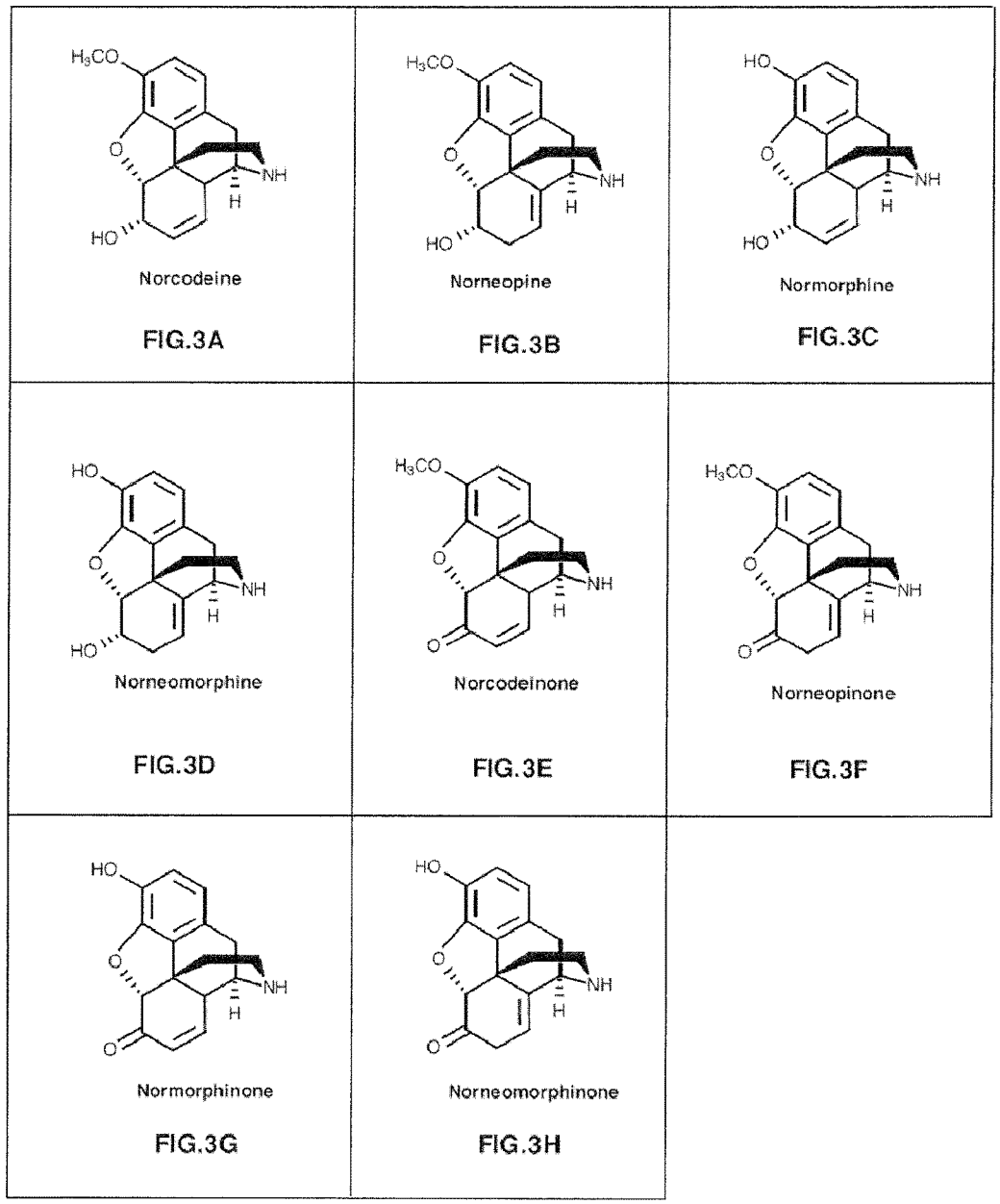
FIG. 3 depicts the chemical structures of certain morphinans, notably, morphinans having a hydrogenated $N_{17}$: norcodeine (FIG. 3A), norneopine (FIG. 3B) normorphine (FIG. 3C), norneomorphine (FIG. 3D), norcodeinone (FIG. 3E), norneopinone (FIG. 3F), normorphinone (FIG. 3G), norneomorphinone (FIG. 3H).

The term "norcodeine" as used herein refers to a chemical compound having the structure set forth in FIG. 3A.

The term "norneopine" as used herein refers to a chemical compound having the structure set forth in FIG. 3B.

The term "normorphine" as used herein refers to a chemical compound having the structure set forth in FIG. 3C.

The term "norneomorphine" as used herein refers to a chemical compound having the structure set forth in FIG. 3D.

The term "norcodeinone" as used herein refers to a chemical compound having the structure set forth in FIG. 3E.

The term "norneopinone" as used herein refers to a chemical compound having the structure set forth in FIG. 3F.

The term "normorphinone" as used herein refers to a chemical compound having the structure set forth in FIG. 3G.

The term "norneomorphinone" as used herein refers to a chemical compound having the structure set forth in FIG. 3H.

Figure 4:
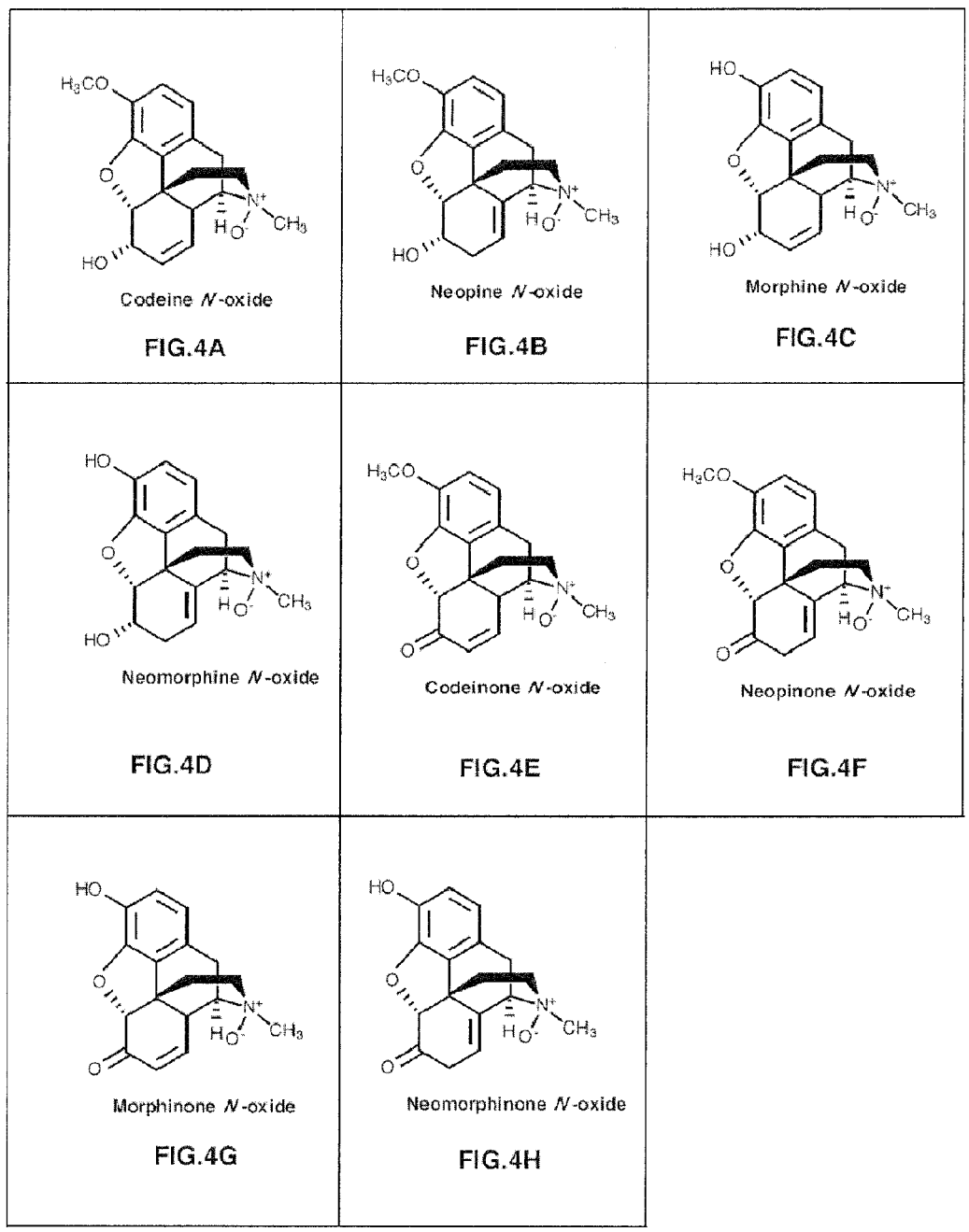
FIG. 4 depicts the chemical structures of certain morphinans, notably morphinans having a methylated N-oxidized $N_{17}$: codeine N-oxide (FIG. 4A), neopine N-oxide (FIG. 4B), morphine N-oxide (FIG. 4C), neomorphine N-oxide (FIG. 4D), codeinone N-oxide (FIG. 4E), neopinone N-oxide (FIG. 4F), morphinone N-oxide (FIG. 4G) and neomorphinone N-oxide (FIG. 4H).

The term "codeine N-oxide" as used herein refers to a chemical compound having the structure set forth in FIG. 4A.

The term "neopine N-oxide" as used herein refers to a chemical compound having the structure set forth in FIG. 4B.

The term "morphine N-oxide" as used herein refers to a chemical compound having the structure set forth in FIG. 4C.

The term "neomorphine N-oxide" as used herein refers to a chemical compound having the structure set forth in FIG. 4D.

The term "codeinone N-oxide" as used herein refers to a chemical compound having the structure set forth in FIG. 4E.

The term "neopinone N-oxide" as used herein refers to a chemical compound having the structure set forth in FIG. 4F.

The term "morphinone N-oxide" as used herein refers to a chemical compound having the structure set forth in FIG. 4G.

The term "neomorphinone N-oxide" as used herein refers to a chemical compound having the structure set forth in FIG. 4H.

The term "oxo group" means a group represented by "C=O".

The term "morphinan substrate" is any codeine isomerase or codeinone reductase substrate molecule, or precursor molecule thereof, that may be exogenously or endogenously provided to perform, in vivo or in vitro, a reaction which results in the conversion of the first morphinan into the second morphinan. In respect of the performance of in vitro reactions the morphinan substrate may be a first morphinan selected from the morphinans set forth in FIGS. 2A, 2C, 2E, 2G, 3A, 3C, 3E, 3G, 4A, 4C, 4E and 4G. In respect of the performance of in vivo reactions the morphinan substrate may be first morphinan selected from the morphinans set forth in FIGS. 2A, 2C, 2E, 2G, 3A, 3C, 3E, 3G, 4A, 4C, 4E and 4G, and furthermore the first morphinan may be a precursor of a first morphinan which can be metabolized by the cell to form one of the morphinans set forth in FIGS. 2A, 2C, 2E, 2G, 3A, 3C, 3E, 3G, 4A, 4C, 4E and 4G.

The terms "codeine isomerase" and "neopinone reductase", which may be used interchangeably herein, refer to any and all enzymes comprising a sequence of amino acid residues which is (i) substantially identical to the amino acid sequences constituting any codeine isomerase polypeptide set forth herein, including, for example, SEQ. ID NO: 2, or (ii) encoded by a nucleic acid sequence capable of hybridizing under at least moderately stringent conditions to any nucleic acid sequence encoding any codeine isomerase polypeptide set forth herein, but for the use of synonymous codons.

The term "codeinone reductase" refers to any and all enzymes comprising a sequence of amino acid residues which is (i) substantially identical to the amino acid sequences constituting any codeinone reductase polypeptide set forth herein, including, for example, SEQ. ID NO: 10, or (ii) encoded by a nucleic acid sequence capable of hybridizing under at least moderately stringent conditions to any nucleic acid sequence encoding any codeinone reductase polypeptide set forth herein, but for the use of synonymous codons.

The term "6-O-demethylase" refers to any and all enzymes comprising a sequence of amino acid residues which is (i) substantially identical to the amino acid sequences constituting any 6-O-demethylase polypeptide set forth herein, including, for example, SEQ. ID NO: 22, or (ii) encoded by a nucleic acid sequence capable of hybridizing under at least moderately stringent conditions to any nucleic acid sequence encoding any 6-O-demethylase polypeptide set forth herein, but for the use of synonymous codons.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil, and xanthine and hypoxanthine.

The term "nucleic acid sequence encoding codeine isomerase", "nucleic acid sequence encoding a codeine isomerase polypeptide", nucleic acid sequence encoding a neopinone reductase" and "nucleic acid sequence encoding a neopinone reductase polypeptide" refer to any and all nucleic acid sequences encoding a codeine isomerase polypeptide, including, for example, SEQ. ID NO: 1. Nucleic acid sequences encoding a codeine isomerase polypeptide further include any and all nucleic acid sequences which (i) encode polypeptides that are substantially identical to the codeine isomerase polypeptide sequences set forth herein; or (ii) hybridize to any codeine isomerase nucleic acid sequences set forth herein under at least moderately stringent hybridization conditions or which would hybridize thereto under at least moderately stringent conditions but for the use of synonymous codons.

The term "nucleic acid sequence encoding codeinone reductase", "nucleic acid sequence encoding a codeinone reductase polypeptide", refer to any and all nucleic acid sequences encoding a codeinone reductase polypeptide, including, for example, SEQ. ID NO: 5. Nucleic acid sequences encoding a codeinone reductase polypeptide further include any and all nucleic acid sequences which (i) encode polypeptides that are substantially identical to the codeinone reductase polypeptide sequences set forth herein; or (ii) hybridize to any codeinone reductase nucleic acid sequences set forth herein under at least moderately stringent hybridization conditions or which would hybridize thereto under at least moderately stringent conditions but for the use of synonymous codons.

The term "nucleic acid sequence encoding 6-O-demethylase", "nucleic acid sequence encoding a 6-O-demethylase polypeptide", refer to any and all nucleic acid sequences encoding a codeinone reductase polypeptide, including, for example, SEQ. ID NO: 21. Nucleic acid sequences encoding a 6-O-demethylase polypeptide further include any and all nucleic acid sequences which (i) encode polypeptides that are substantially identical to the 6-O-demethylase polypeptide sequences set forth herein; or (ii) hybridize to any 6-O-demethylase nucleic acid sequences set forth herein under at least moderately stringent hybridization conditions or which would hybridize thereto under at least moderately stringent conditions but for the use of synonymous codons.

By the term "substantially identical" it is meant that two polypeptide sequences preferably are at least 70% identical, and more preferably are at least 85% identical and most preferably at least 95% identical, for example 96%, 97%, 98% or 99% identical. In order to determine the percentage of identity between two polypeptide sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "chimeric" as used herein in the context of nucleic acid sequences refers to at least two linked nucleic acid sequences which are not naturally linked. Chimeric nucleic acid sequences include linked nucleic acid sequences of different natural origins. For example a nucleic acid sequences constituting a yeast promoter linked to a nucleic acid sequence encoding a codeine isomerase or codeinone reductase protein is considered chimeric. Chimeric nucleic acid sequences also may comprise nucleic acid sequences of the same natural origin, provided they are not naturally linked. For example a nucleic acid sequence constituting a promoter obtained from a particular cell-type may be linked to a nucleic acid sequence encoding a polypeptide obtained from that same cell-type, but not normally linked to the nucleic acid sequence constituting the promoter. Chimeric nucleic acid sequences also include nucleic acid sequences comprising any naturally occurring nucleic acid sequences linked to any non-naturally occurring nucleic acid sequence.

The terms "substantially pure" and "isolated", as may be used interchangeably herein describe a compound, e.g., a morphinan or a polypeptide, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

The term "functional variant" as used herein in reference to nucleic acid sequences or polypeptide sequences refers to nucleic acid sequences or polypeptide sequences capable of performing the same function as one a noted nucleic acid sequence or polypeptide sequence. Thus, for example, a functional variant of the codeine isomerase polypeptide set forth in SEQ. ID NO: 2, refers to a polypeptide capable of performing the same function as the polypeptide set forth in SEQ. ID NO: 2.

The term "recovered" as used herein in association with an enzyme or protein or morphinan refers to a more or less pure form of the enzyme or protein or morphinan.

The term "in vivo" as used herein to describe methods of making morphinans refers to contacting a first morphinan with an enzyme capable of catalyzing conversion of a first morphinan within a living cell, including, for example, a microbial cell or a plant cell, to form a second morphinan.

The term "in vitro" as used herein to describe methods of making morphinans refers to contacting a first morphinan with an enzyme capable of catalyzing conversion of the first morphinan in an environment outside a living cell, including, without limitation, for example, in a microwell plate, a tube, a flask, a beaker, a tank, a reactor and the like, to form a second morphinan.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

General Implementation

As hereinbefore mentioned, the present disclosure relates to certain alkaloids belonging to the class of chemical compounds known as morphinans. The current disclosure further relates to certain enzymes capable of catalyzing reactions resulting in the conversion of a first morphinan into a second morphinan. The herein provided methods represent a novel and efficient means of making certain morphinans, including, in a preferred embodiment, neopine. The methods provided herein do not rely on chemical synthesis of the subject morphinans and may be conducted at commercial scale. To the best of the inventor's knowledge, the current disclosure provides for the first time a methodology to manufacture certain morphinans, including neopine, using living cells not normally capable of synthesizing such morphinans. Such cells may be used as a source whence these morphinans may economically be extracted. The morphinans produced in accordance with the present disclosure are useful inter alia in the manufacture of pharmaceutical compositions.

Accordingly, the present disclosure provides, in at least one aspect, a method of making a second morphinan having a $C_7$-$C_8$ saturated carbon bond and a $C_8$-$C_{14}$ mono-unsaturated carbon bond comprising:

(a) providing a first morphinan having a $C_7$-$C_8$ mono-unsaturated carbon bond and a $C_8$-$C_{14}$ saturated carbon bond; and (b) contacting the first morphinan with a codeine isomerase capable of converting the first morphinan into the second morphinan.

In preferred embodiments the method further comprises a step (c) recovering the second morphinan.

In preferred embodiments, the first morphinan and the second morphinan each possess a bridging oxygen atom between carbon atoms $C_4$ and $C_5$ forming a tetrahydrofuranyl ring within the morphinan structure, thus having the prototype chemical structure shown in FIG. 1B.

The present disclosure provides, in at least one aspect, a method of making a morphinan comprising:

(b) providing a first morphinan;

(b) contacting the first morphinan with a codeine isomerase or codeinone reductase capable of converting the first morphinan under conditions that permit the conversion of the first morphinan into the second morphinan;

wherein the first morphinan has the chemical formula (I):

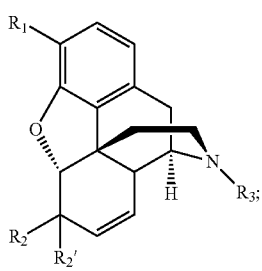

and wherein the second morphinan has the chemical formula (II):

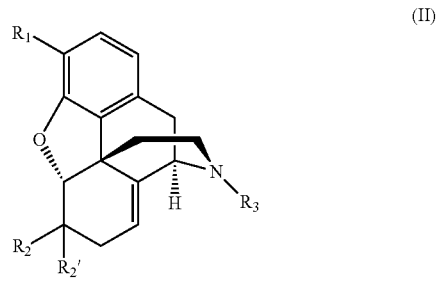

wherein, in the first and the second morphinan, $R_1$ represents a hydroxyl group or a methoxy group; wherein in the first and the second morphinan $R_2$ represents a hydroxyl group and $R_2'$ represents a hydrogen atom, or taken together, $R_2$ and $R_2'$ form an oxo group; and wherein in the first and the second morphinan $R_3$ represents a hydrogen atom, or a methyl group, wherein when $R_3$ represents a methyl group, the nitrogen atom bonded to $R_3$ is optionally in the form of an N-oxide.

Synthesis of Morphinans Comprising a Methylated $N_{17}$

In preferred embodiments hereof, the $N_{17}$ of the first and second morphinan are methylated, as shown in compounds (V) and (VI), respectively:

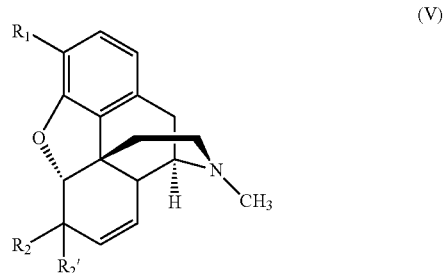

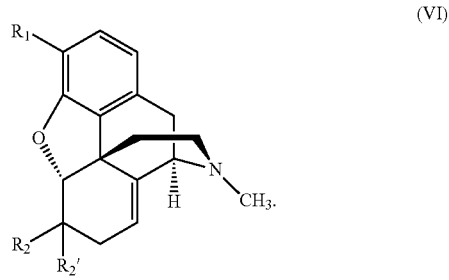

In a further preferred embodiment, in the first and second morphinan the $N_{17}$ is methylated, and $R_1$ is a methoxy group, $R_2$ is a hydroxyl group and $R_2'$ is a hydrogen atom, providing codeine (compound (III)) for the first morphinan and neopine (compound (IV)) for the second morphinan.

In a further preferred embodiment, in the first and second morphinan the $N_{17}$ is methylated, and $R_1$ is a hydroxyl group, $R_2$ is a hydroxyl group and $R_2'$ is a hydrogen atom, providing morphine for the first morphinan and neomorphine for the second morphinan.

In a further preferred embodiment, in the first and second morphinan the $N_{17}$ is methylated, and $R_1$ is a methoxy group, and taken together, $R_2$ and $R_2'$ form an oxo group, providing codeinone for the first morphinan and neopinone for the second morphinan.

In a further preferred embodiment, in the first and second morphinan the $N_{17}$ is methylated, and $R_1$ is a hydroxyl group, and taken together, $R_2$ and $R_2'$ form an oxo group, providing morphinone for the first morphinan and neomorphinone for the second morphinan.

It is noted that in each of the foregoing embodiments, $R_1$ in the first morphinan is identical to $R_1$ in the second morphinan. Similarly, $R_2$ and $R_2'$ in the first morphinan are identical to $R_2$ and $R_2'$ in the second morphinan.

Synthesis of Morphinans Comprising a Hydrogenated $N_{17}$

In preferred embodiments hereof, the $N_{17}$ of the first and second morphinan are hydrogenated as shown in compounds (VII) and (VIII), respectively:

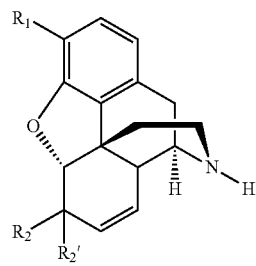

(VII)

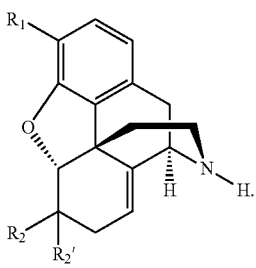

(VIII)

In a further preferred embodiment, in the first and second morphinan the $N_{17}$ is hydrogenated, and $R_1$ is a methoxy group, $R_2$ is a hydroxyl group and $R_2'$ is a hydrogen atom, providing norcodeine for the first morphinan and norneopine for the second morphinan.

In a further preferred embodiment, in the first and second morphinan the $N_{17}$ is hydrogenated, and $R_1$ is a hydroxyl group, $R_2$ is a hydroxyl group and $R_2'$ is a hydrogen atom, providing normorphine for the first morphinan and norneomorphine for the second morphinan.

In a further preferred embodiment, in the first and second morphinan the $N_{17}$ is hydrogenated, and $R_1$ is a methoxy group, and taken together, $R_2$ and $R_2'$ form an oxo group, providing norcodeinone for the first morphinan and norneopinone for the second morphinan.

In a further preferred embodiment, in the first and second morphinan the $N_{17}$ is hydrogenated, and $R_1$ is a hydroxyl group, and taken together $R_2$ and $R_2'$ form an oxo group, providing normorphinone for the first morphinan and norneomorphinone for the second morphinan.

It is noted that in each of the foregoing embodiments, $R_1$ in the first morphinan is identical to $R_1$ in the second morphinan. Similarly, $R_2$ and $R_2'$ in the first morphinan are identical to $R_2$ and $R_2'$ in the second morphinan.

Synthesis of Morphinans Comprising a Methylated and N-Oxidized $N_{17}$.

In preferred embodiments hereof, the $N_{17}$ of the first and second morphinan are methylated and N-oxidized as shown in compounds (IX) and (X), respectively:

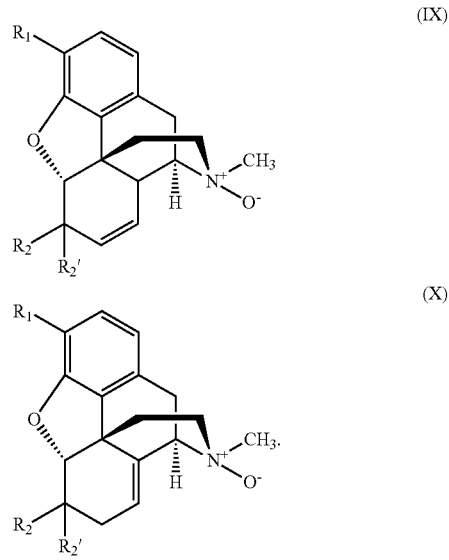

In a further preferred embodiment, in the first and second morphinan the $N_{17}$ is methylated and N-oxidized, and $R_1$ is a methoxy group, $R_2$ is a hydroxyl group and $R_2'$ is a hydrogen atom, providing codeine N-oxide for the first morphinan and neopine N-oxide for the second morphinan.

In a further preferred embodiment, in the first and second morphinan the $N_{17}$ is methylated and N-oxidized, and $R_1$ is a hydroxyl group, $R_2$ is a hydroxyl group and $R_2'$ is a hydrogen atom, providing morphine N-oxide for the first morphinan and neomorphine N-oxide for the second morphinan.

In a further preferred embodiment, in the first and second morphinan the $N_{17}$ is methylated and N-oxidized, and $R_1$ is a methoxy group, and taken together $R_2$ and $R_2'$ form an oxo group, providing codeinone N-oxide for the first morphinan and neopinone N-oxide for the second morphinan.

In a further preferred embodiment, in the first and second morphinan the $N_{17}$ is methylated and N-oxidized, and $R_1$ is a hydroxyl group, and taken together $R_2$ and $R_2'$ form an oxo group, providing morphinone N-oxide for the first morphinan and neomorphinone N-oxide for the second morphinan.

It is noted that in each of the foregoing embodiments, $R_1$ in the first morphinan is identical to $R_1$ in the second morphinan. Similarly, $R_2$ and $R_2'$ in the first morphinan are identical to $R_2$ and $R_2'$ in the second morphinan.

In order to convert the first morphinan to the second morphinan, the first morphinan is contacted with a codeine isomerase or a codeinone reductase under reaction conditions that permit the conversion of the first morphinan to the second morphinan. The codeine isomerase may be any codeine isomerase capable of converting the first morphinan to the second morphinan, including in preferred embodiments the codeine isomerase set forth in SEQ. ID NO: 2, and functional variants thereof. The codeinone reductase may be any codeinone reductase capable of converting the first morphinan to the second morphinan, including in preferred embodiments the codeinone reductase set forth in SEQ. ID NO: 10, and functional variants thereof. The reaction conditions may be any reaction conditions that permit the catalysis. The reaction conditions include in vivo or in vitro conditions, as hereinafter further detailed. The reaction conditions further typically include the presence of water and buffering agents, and the reaction is preferably conducted at neutral pH or mild basic pH (from approximately pH 7.5 to approximately pH 9.5). Further typically included are a reducing agent or an oxidizing agent. In particularly preferred embodiments, the oxidizing agent may be nicotine amide adenine dinucleotide phosphate (NAPP$^+$). In further particularly preferred embodiments, the reducing agent is the reduced form of nicotine amide adenine dinucleotide phosphate (NADPH). In embodiments hereof, where codeine isomerase is used, when the reaction is conducted using NADP$^+$, the pH is preferably selected to be approximately 7.5. When the reaction is conducted using NADPH, the pH is preferably selected to be approximately 9.0.

In certain embodiments, the first morphinan may be converted to the second morphinan via one or more intermediate morphinan compounds, wherein such intermediate morphinan compounds are morphinan compounds other than the first or second morphinan compound. In certain embodiments, the intermediate morphinan compound is a furanyl-morphinan, and the furanyl-morphinan is a compound other than the first or second morphinan. In certain embodiments, the intermediate morphinan has the chemical formula (XI):

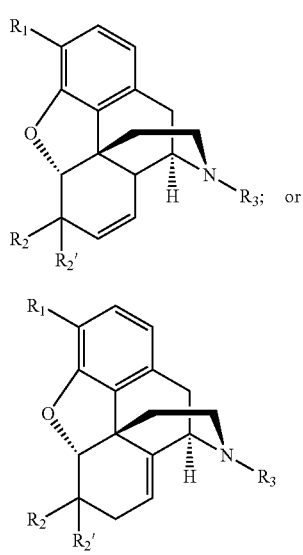

wherein in each formula (XI) and (XII): $R_1$ represents a hydroxyl group or a methoxy group; $R_2$ represents a hydroxyl group and $R_2'$ represents a hydrogen atom, or taken together, $R_2$ and $R_2'$ form an oxo group; and $R_3$ represents a hydrogen atom, or a methyl group, wherein when $R_3$ represents a methyl group, the nitrogen atom bonded to $R_3$ is optionally in the form of an N-oxide, and wherein the intermediate morphinan compound is a compound other than the first or second morphinan compound.

The time period during which an intermediate morphinan compound exists may vary and may depend on the reaction conditions selected. Furthermore an equilibrium between the first morphinan, second morphinan and an intermediate morphinan compound may form wherein the reaction may comprise various amounts of the first morphinan, the second morphinan and, optionally, one or more intermediate morphinan compounds. The relative amounts of each of these compounds may vary depending on the reaction conditions selected. In general, in accordance herewith the molar fraction of the second morphinan, upon substantial completion of the reaction, is at least 50%, at least 60%, at least 70%, at least 80%, at least 90%, at least, 95%, at least 99% or at least 99.9%.

Figure 13:
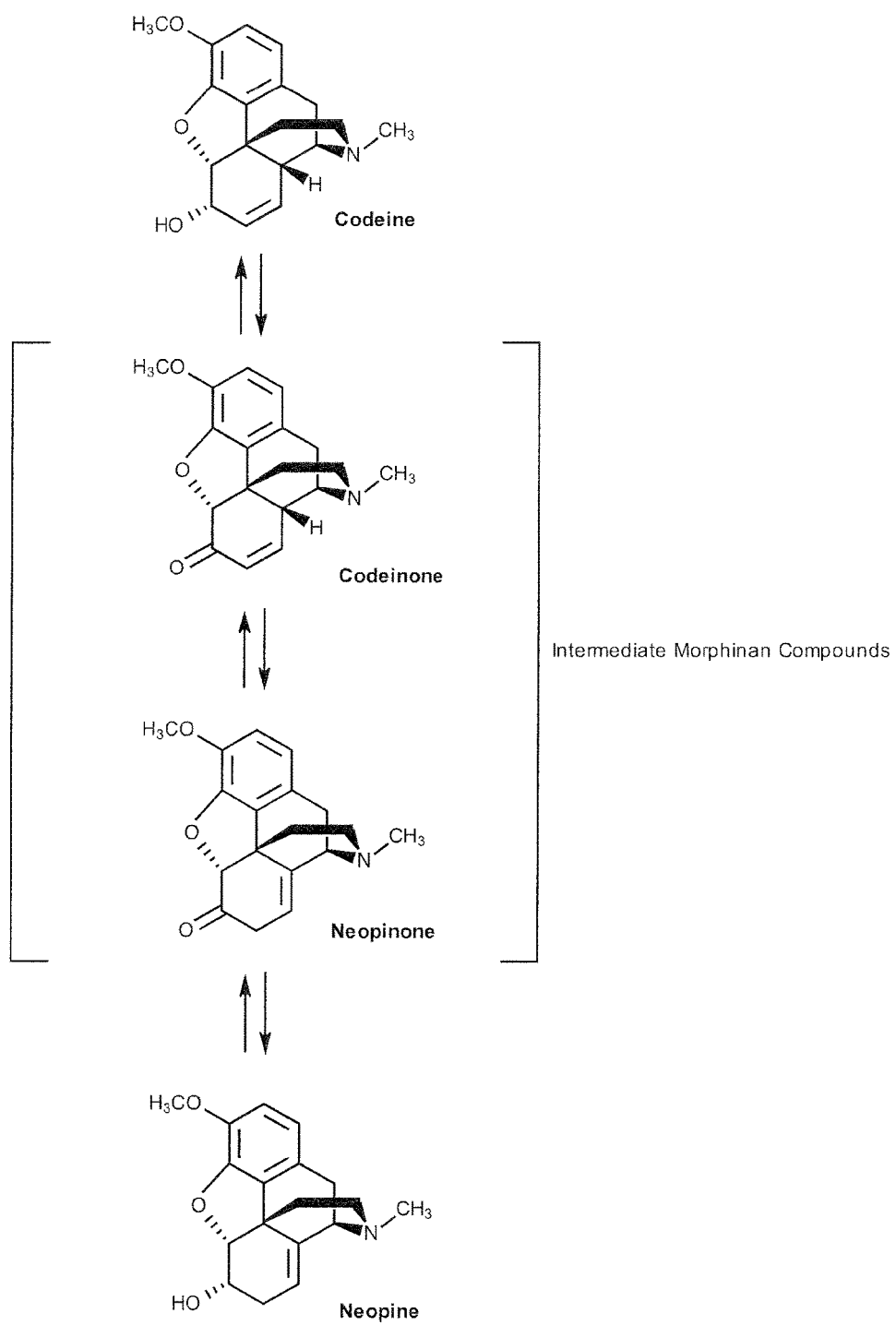
FIG. 13 depicts a chemical reaction involving the conversion of codeine to neopine via intermediate morphinan compounds, neopinone and codeinone.

In certain embodiments, the first morphinan is codeine and the second morphinan is neopine, and codeinone and neopinone are formed, as a first and second intermediate morphinan compound, respectively. The foregoing embodiment is further illustrated in FIG. 13. In embodiments hereof where one or more intermediate morphinan compounds are formed, no enzymes other than codeine isomerase or codeinone reductase are required to perform the reaction. Thus in accordance herewith, the conversion of the first morphinan into the second morphinan occurs in a manner wherein a codeinone reductase or a codeine isomerase are contacted with the first morphinan, and wherein the first morphinan is converted into the second morphinan without enzymatic compounds other than codeinone reductase or codeine isomerase.

In some embodiments, the reaction may be conducted by including in the reaction a precursor molecule of a first morphinan. In some embodiments, the precursor molecule is a morphinan other than the first or second morphinan. In some embodiments, the precursor molecule is a furanyl-morphinan other than the first or second morphinan.

In some embodiments, the precursor molecule has the chemical formula (XIII):

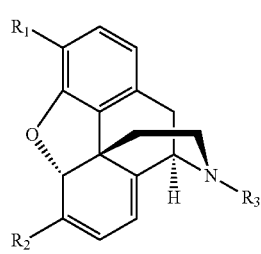

wherein, $R_1$ represents a hydroxyl group or a methoxy group; wherein $R_2$ represents a hydroxyl group or a methoxy group; and wherein $R_3$ represents a hydrogen atom, or a methyl group, wherein when $R_3$ represents a methyl group the nitrogen atom bonded to $R_3$ is optionally in the form of an N-oxide, and wherein precursor molecule is a molecule other than the first or second morphinan.

In further embodiments, the reaction may be conducted by including in the reaction a precursor molecule of a first morphinan and one or more enzymes capable of converting the precursor molecule of the first morphinan into the first morphinan.

In embodiments encompassing the inclusion of a precursor molecule of a first morphinan, the conversion of a precursor molecule into the first morphinan may proceed via one or more intermediate precursor molecules.

In some embodiments, the intermediate precursor molecule is a morphinan other than the first or the second morphinan. In some embodiments, the intermediate precursor molecule is a furanyl-morphinan, other than the first or second morphinan.

In some embodiments, the intermediate precursor molecule has the chemical formula (XI) or (XII), wherein in each formula (XI) and (XII): $R_1$ represents a hydroxyl group or a methoxy group; $R_2$ represents a hydroxyl group and $R_2'$ represents a hydrogen atom, or taken together, $R_2$ and $R_2'$ form an oxo group; and $R_3$ represents a hydrogen atom, or a methyl group, wherein when $R_3$ represents a methyl group, the nitrogen atom bonded to $R_3$ is optionally in the form of an N-oxide, and wherein the intermediate precursor molecule is a morphinan other than the first or second morphinan.

Figure 14:
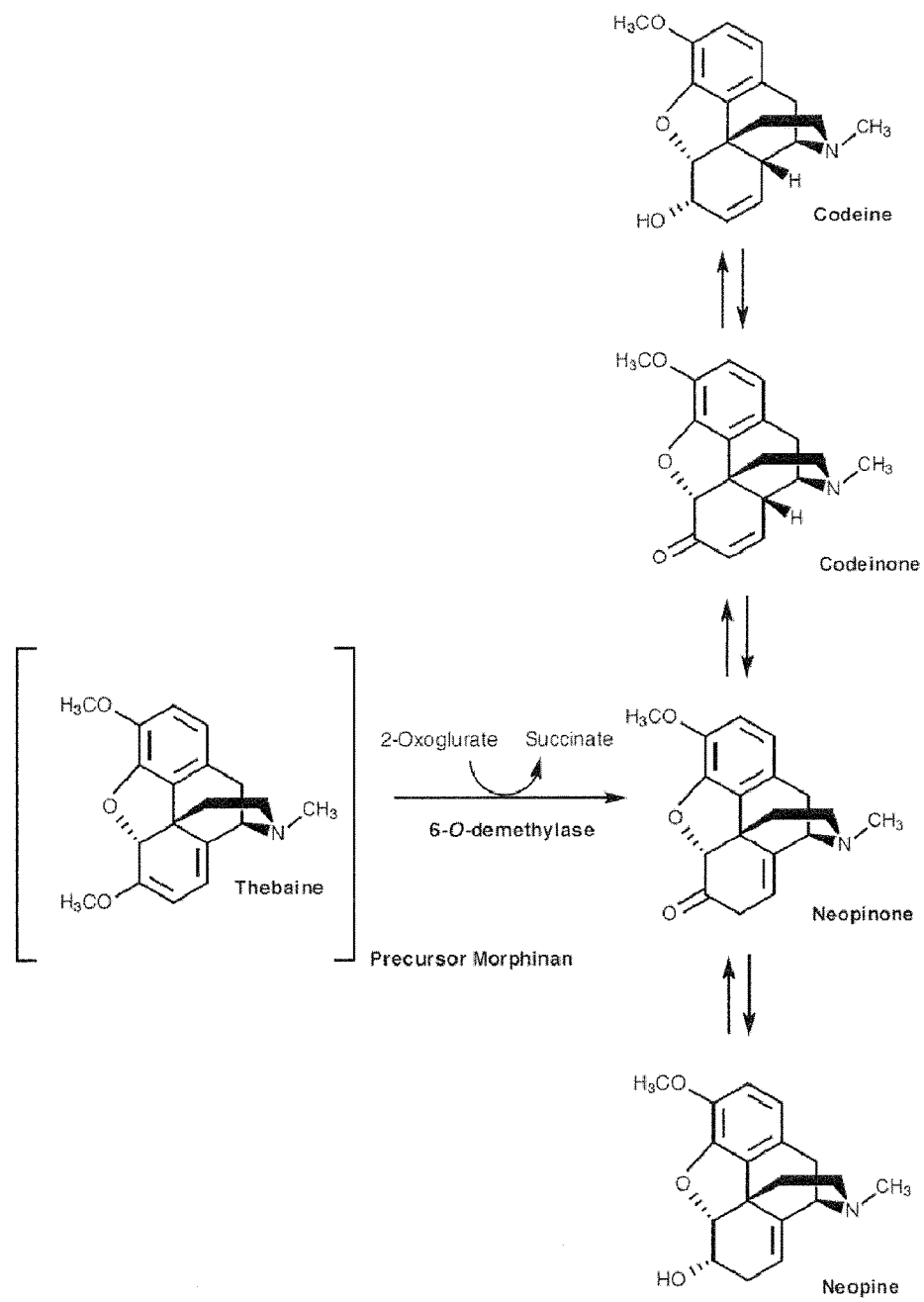
FIG. 14 depicts a chemical reaction involving the conversion of neopine from codeine using thebaine as a codeine precursor compound, and codeinone and neopinone as intermediate precursor compounds.

In certain embodiments, the reaction may include a morphinan other than the first or the second morphinan, wherein the morphinan other than the first morphinan or the second morphinan is thebaine. In this embodiment, the reaction may further include a demethylase, for example an O-demethylase, capable of demethylating thebaine, including the 6-O-demethylase set forth in SEQ. ID NO: 22. In this embodiment, the precursor molecule, thebaine, may be converted into the intermediate precursor molecules neopinone and codeinone. This embodiment of the present disclosure is further illustrated in FIG. 14.

In certain embodiments, the reaction may include a morphinan other than the first or the second morphinan, wherein the morphinan other than the first morphinan or the second morphinan is oripavine. In this embodiment, the reaction may further include a demethylase, for example an O-demethylase, capable of demethylating oripavine. In this embodiment the precursor molecule, oripavine may be converted into the intermediate precursor molecules, neomorphinone and morphinone.

In certain embodiments, mixtures of enzymes may be used mixtures of two or more codeinone reductases, or two or more codeine isomerases, or a codeinone reductase and a codeine isomerase.

Thus it will be clear from the foregoing that the present disclosure includes embodiments wherein the first morphinan is provided by providing a precursor molecule to the first morphinan, and one or more enzymes capable of converting the precursor molecule into the first morphinan. This embodiment is further illustrated in Examples 2 and 3.

In other embodiments, the first morphinan is provided substantially free of other morphinans, including substantially free from precursor molecules to the first morphinan, and/or substantially free of enzymes capable of converting a precursor molecule to the first morphinan into the first morphinan.

In Vitro Synthesis of Morphinans

In accordance with certain aspects of the present disclosure, a first morphinan is brought in contact with catalytic quantities of the enzyme codeine isomerase or codeinone reductase under reaction conditions permitting an enzyme catalyzed chemical conversion of the first morphinan under in vitro reaction conditions. Under such in vitro reaction conditions the initial reaction constituents are provided in more or less pure form and are mixed under conditions that permit the chemical reaction to substantially proceed.

Substantially pure forms of the first morphinan may be purchased as a substantially pure chemical compound, chemically synthesized from precursor compounds, or isolated from natural sources including *Papaver somniferum*. Other plant species that may be used in accordance herewith to obtain the first morphinan include, without limitation, plant species belonging to the plant families of Eupteleaceae, Lardizabalaceae, Circaeasteraceae, Menispermaceae, Berberidaceae, Ranunculaceae, and Papaveraceae (including those belonging to the subfamilies of Pteridophylloideae, Papaveroideae and Fumarioideae) and further includes plants belonging to the genus *Argemone*, including *Argemone mexicana* (Mexican Prickly Poppy), plants belonging to the genus *Berberis*, including *Berberis thunbergii* (Japanese Barberry), plants belonging to the genus *Chelidonium*, including *Chelidonium majus* (Greater Celandine), plants belonging to the genus *Cissampelos*, including *Cissampelos mucronata* (Abuta), plants belonging to the genus *Cocculus*, including *Cocculus trilobus* (Korean Moonseed), plants belonging to the genus *Corydalis*, including *Corydalis chelanthifolia* (Ferny Fumewort), *Corydalis cava; Corydalis ochotenis; Corydalis ophiocarpa; Corydalis platycarpa; Corydalis tuberosa*; and *Cordyalis bulbosa*, plants belonging to the genus *Eschscholzia*, including *Eschscholzia californica* (California Poppy), plants belonging to the genus *Glaucium*, including *Glaucium flavum* (Yellowhorn Poppy), plants belonging to the genus *Hydrastis*, including *Hydrastis canadensis* (Goldenseal), plants belonging to the genus *Jeffersonia*, including *Jeffersonia diphylla* (Rheumatism Root), plants belonging to the genus *Mahonia*, including *Mahonia aquifolium* (Oregon Grape), plants belonging to the genus *Menispermum*, including *Menispermum canadense* (Canadian Moonseed), plants belonging to the genus *Nandina*, including *Nandina domestica* (Sacred Bamboo), plants belonging to the genus *Nigella*, including *Nigella sativa* (Black Cumin), plants belonging to the genus *Papaver*, including *Papaver bracteatum* (Persian Poppy), *Papver sommferum, Papaver cylindricum, Papaver decaisnei, Papaver fugax, Papaver nudicale, Papaver oreophyllum, Papaver orientale, Papaver paeomfolium, Papaver persicum, Papaver pseudo-orientale, Papaver rhoeas, Papaver rhopalothece, Papaver armeniacum, Papaver setigerum, Papaver tauricolum*, and *Papaver triniaefolium*, plants belonging to the genus *Sanguinaria*, including *Sanguinaria canadensis* (Bloodroot), plants belonging to the genus *Stylophorum*, including *Stylophorum diphyllum* (Celandine Poppy), plants belonging to the genus *Thalictrum*, including *Thalictrum flavum* (Meadow Rue), plants belonging to the genus *Tinospora*, including *Tinospora cordifolia* (Heartleaf Moonseed), plants belonging to the genus *Xanthoriza*, including *Xanthoriza simplicissima* (Yellowroot) and plants belonging to the genus *Romeria* including *Romeria carica*.

More or less pure forms of the codeine isomerase enzyme or codeinone reductase may be obtained by isolation of these enzymes from natural sources, including, but not limited to, *Papaver somniferum, Papaver bracteatum, Papaver nudicale, Papaver orientale* and *Papaver rhoeas*, or the enzymes may be prepared recombinantly, or synthetically. Thus provided herein is further a method for preparing a codeine isomerase or a codeinone reductase comprising:

(a) providing a chimeric nucleic acid molecule comprising as operably linked components:
  (i) a nucleic acid sequence encoding a codeine isomerase or codeinone reductase; and
  (ii) one or more a nucleic acid sequences capable of controlling expression in a host cell;
(b) introducing the chimeric nucleic acid molecule into a host cell and growing the host cell to produce the codeine isomerase or codeinone reductase; and
(c) recovering the codeine isomerase or codeinone reductase polypeptide from the host cell.

The nucleic acid sequence encoding codeine isomerase or codeinone reductase may be obtained from *Papaver somniferum*. Other plant species from which a nucleic acid encoding a codeine isomerase or codeinone reductase may be obtained in accordance herewith include, without limitation, plant species belonging to the plant families of Eupteleaceae, Lardizabalaceae, Circaeasteraceae, Menispermaceae, Berberidaceae, Ranunculaceae, and Papaveraceae (including those belonging to the subfamilies of Pteridophylloideae, Papaveroideae and Fumarioideae) and further includes plants belonging to the genus *Argemone*, including *Argemone mexicana* (Mexican Prickly Poppy), plants belonging to the genus *Berberis*, including *Berberis thunbergii* (Japanese Barberry), plants belonging to the genus *Chelidonium*, including *Chelidonium majus* (Greater Celandine), plants belonging to the genus *Cissampelos*, including *Cissampelos mucronata* (Abuta), plants belonging to the genus *Cocculus*, including *Cocculus trilobus* (Korean Moonseed), plants belonging to the genus *Corydalis*, including *Corydalis* chelanthifolia (Ferny Fumewort), *Corydalis cava; Corydalis ochotenis; Corydalis ophiocarpa; Corydalis platycarpa; Corydalis tuberosa*; and *Cordyalis bulbosa*, plants belonging to the genus *Eschscholzia*, including *Eschscholzia californica* (California Poppy), plants belonging to the genus *Glaucium*, including *Glaucium flavum* (Yellowhorn Poppy), plants belonging to the genus *Hydrastis*, including *Hydrastis canadensis* (Goldenseal), plants belonging to the genus *Jeffersonia*, including *Jeffersonia diphylla* (Rheumatism Root), plants belonging to the genus *Mahonia*, including *Mahonia aquifolium* (Oregon Grape), plants belonging to the genus *Menispermum*, including *Menispermum canadense* (Canadian Moonseed), plants belonging to the genus *Nandina*, including *Nandina domestica* (Sacred Bamboo), plants belonging to the genus *Nigella*, including *Nigella sativa* (Black Cumin), plants belonging to the genus *Papaver*, including *Papaver bracteatum* (Persian Poppy), *Papver somniferum, Papaver cylindricum, Papaver decaisnei, Papaver fugax, Papaver nudicale, Papaver oreophyllum, Papaver orientale, Papaver paeonifolium, Papaver persicum, Papaver pseudo-orientale, Papaver rhoeas, Papaver rhopalothece, Papaver armeniacum, Papaver setigerum, Papaver tauricolum*, and *Papaver triniaefolium*, plants belonging to the genus *Sanguinaria*, including *Sanguinaria canadensis* (Bloodroot), plants belonging to the genus *Stylophorum*, including *Stylophorum diphyllum* (Celandine Poppy), plants belonging to the genus *Thalictrum*, including *Thalictrum flavum* (Meadow Rue), plants belonging to the genus *Tinospora*, including *Tinospora cordifolia* (Heartleaf Moonseed), plants belonging to the genus *Xanthoriza*, including *Xanthoriza simplicissima* (Yellowroot) and plants belonging to the genus *Romeria* including *Romeria carica*.

In preferred embodiments, the nucleic acid sequence encoding the codeine isomerase comprises the nucleic acid sequence set forth in SEQ. ID NO: 1.

In preferred embodiments, the nucleic acid sequence encoding the codeinone reductase comprises the nucleic acid sequence set forth in SEQ. ID NO: 5.

In further embodiments, the nucleic acid sequence encoding the codeinone reductase comprises SEQ. ID NO: 3; SEQ. ID NO: 4; SEQ. ID NO: 6; SEQ. ID NO: 7; SEQ. ID NO: 13; SEQ. ID NO: 15; SEQ. ID NO: 17; or SEQ. ID NO: 19.

Growth of the host cells leads to production of the codeine isomerase or codeinone reductase polypeptides. The polypeptides subsequently may be recovered, isolated and separated from other host cell components by a variety of different protein purification techniques including, e.g. ion-exchange chromatography, size exclusion chromatography, affinity chromatography, hydrophobic interaction chromatography, reverse phase chromatography, gel filtration, etc. Further general guidance with respect to protein purification may for example be found in: Cutler, P. Protein Purification Protocols, Humana Press, 2004, Second Ed. Thus substantially pure preparations of the codeine isomerase or codeinone reductase polypeptides may be obtained. The protein preparation thus obtained is capable of catalyzing a chemical reaction resulting into the formation of a second morphinan from a first morphinan. Accordingly, the present disclosure further provides compositions for making a morphinan comprising a polypeptide capable of, in a first morphinan having a mono-unsaturated $C_7$-$C_8$ bond and a saturated $C_8$-$C_{14}$ bond:

(i) saturating the $C_7$-$C_8$ bond; and
(ii) unsaturating the $C_8$-$C_{14}$ bond, to form a second morphinan having a saturated $C_7$-$C_8$ and a mono-unsaturated $C_8$-$C_{14}$ bond.

In accordance herewith in order to perform a reaction under in vitro conditions, a first morphinan is brought in contact with catalytic quantities of codeine isomerase or codeinone reductase, under reaction conditions permitting an enzyme catalyzed chemical conversion of the first morphinan. In preferred embodiments, the agents are brought in contact with each other and mixed to form a mixture. In preferred embodiments the mixture is an aqueous mixture comprising water and further optionally additional agents to facilitate enzyme catalysis, including buffering agents, salts, pH modifying agents. As hereinbefore mentioned it is particularly preferred that the reaction mixture comprises NADPH or $NADP^+$. The reaction may be performed at a range of different temperatures. In preferred embodiments the reaction is performed at a temperature between about 18° C. and 37° C. Upon completion of the in vitro reaction the second morphinan may be obtained in more or less pure form.

In further embodiments, the reaction conditions may be arranged to include one or more enzymes capable of converting a precursor of first morphinan into the first morphinan, as well as the precursor to the first morphinan. Thus in certain embodiments, the reaction conditions may be arranged to include thebaine and a demethylase, capable of forming codeine from thebaine.

In Vivo Synthesis of Morphinans

In accordance with certain aspects of the present disclosure, a first morphinan is brought in contact with catalytic quantities of codeine isomerase or codeinone reductase under reaction conditions permitting an enzyme catalyzed chemical conversion of a first morphinan under in vivo reaction conditions. Under such in vivo reaction conditions living cells are modified in such a manner that they produce a second morphinan. In certain embodiments the living cells are microorganisms, including bacterial cells and fungal cells. In other embodiments the living cells are multicellular organisms, including plants and plant cell cultures.

In one embodiment, the living cells are selected to be host cells not naturally capable of producing the second morphinan. In another embodiment, the cells are able to produce the second morphinan but the levels at which the second morphinan are produced are lower than desirable, and by implementation of the methods of the present disclosure, the cells are modified such that the levels of the second morphinan in the cells are modulated relative to the levels in the unmodified cells. In a specific embodiment, the levels of the second morphinan in the modified cells are higher than the levels in the unmodified cells. Such cells include, without limitation, bacteria, yeast, other fungal cells, plant cells, or animal cells. The produced morphinan may be recovered from the modified cells.

Accordingly, provided herein still further, is a method for preparing a morphinan having chemical formula (II) comprising:
(a) providing a chimeric nucleic acid molecule comprising as operably linked components:
(i) a nucleic acid sequence encoding a codeine isomerase or codeinone reductase polypeptide;

(ii) one or more nucleic acid sequences capable of controlling expression in a host cell;

(b) introducing the chimeric nucleic acid molecule into a host cell that endogenously produces or is exogenously supplied with a morphinan substrate;

(c) growing the host cell to produce codeine isomerase or codeinone reductase and to produce the morphinan having chemical formula (II); and (d) recovering morphinan having chemical formula (II) from the cell; and wherein in formula (II), $R_1$ represents a hydroxyl group or a methoxy group;

wherein $R_2$ represents a hydroxyl group and $R_2'$ represents a hydrogen atom, or taken together, $R_2$ and $R_2'$ form an oxo group; and wherein $R_3$ represents a hydrogen atom, or a methyl group, wherein when $R_3$ represents a methyl group, the nitrogen atom bonded to the $R_3$ is optionally in the form of an N-oxide.

In preferred embodiments, the nucleic acid sequence encoding codeine isomerase is the sequence set forth herein as SEQ. ID NO: 1 or a functional variant thereof. In further preferred embodiments, the codeine isomerase is the polypeptide having the sequence set forth in SEQ. ID NO: 2, or a functional variant thereof.

In preferred embodiments, the nucleic acid sequence encoding codeinone reductase is the sequence set forth herein as SEQ. ID NO: 5 or a functional variant thereof. In further preferred embodiments, the codeinone reductase is the polypeptide having the sequence set forth in SEQ. ID NO: 10, or a functional variant thereof.

In further preferred embodiments, the nucleic acid sequence encoding codeinone reductase is the sequence set forth herein as SEQ. ID NO: 3; SEQ. ID NO: 4; SEQ. ID NO: 6; SEQ. ID NO: 7; SEQ. ID NO: 13; SEQ. ID NO: 15; SEQ. ID NO: 17; or SEQ. ID NO: 19, or a functional variant thereof. In further preferred embodiments, the codeinone reductase is the polypeptide having the sequence set forth in SEQ. ID NO: 8; SEQ. ID NO: 9; SEQ. ID NO: 11; SEQ. ID NO: 12; SEQ. ID NO: 14; SEQ. ID NO: 16; SEQ. ID NO: 18; or SEQ. ID NO: 20.

Referring to FIG. 6, in further preferred embodiments, the codeine isomerase that is used in accordance herewith is a codeine isomerase having a sequence substantially identical to SEQ. ID NO: 2 provided however, that such codeine isomerase has the following amino acid residues (AAs) in the denoted positions (wherein each of the positions is numbered consecutively from the N-terminus of the polypeptide chain): (1) AA25=valine; (2) AA29=glutamic acid; (3) AA58=threonine (4) AA178=threonine; (5) AA180=asparagine; (6) AA181=serine; (7) AA219=valine; (8) AA 220=glycine; (9) AA222=alanine; (10) AA225=threonine; (11) AA230=histidine; (12) AA268=alanine; (13) AA285=aspartic acid; (14) AA 301=alanine; (15) AA318=glycine; (16) AA319=glutamic acid; and (17) AA320=valine.

In further preferred embodiments, the codeine isomerase is codeine isomerase having a sequence substantially identical to SEQ. ID NO: 2, provided however, that the codeine isomerase comprises at least 16, at least 15, at least 14, at least 13, at least 12, at least 11, at least 10, at least 9, at least 8, at least 7, at least 6, at least 5, at least 4, at least 3, at least 2, or at least 1 of the following amino acids in the denoted positions (1) AA25=valine; (2) AA29=glutamic acid; (3) AA58=threonine (4) AA178=threonine; (5) AA180=asparagine; (6) AA181=serine; (7) AA219=valine; (8) AA 220=glycine; (9) AA222=alanine; (10) AA225=threonine; (11) AA230=histidine; (12) AA268=alanine; (13) AA285=aspartic acid; (14) AA 301=alanine; (15) AA318=glycine; (16) AA319=glutamic acid; and (17) AA320=valine.

The cells may be capable of endogenously producing a morphinan having chemical formula (I) wherein $R_1$ represents a hydroxyl group or a methoxy group; wherein $R_2$ represents a hydroxyl group and $R_2'$ represents a hydrogen atom, or taken together, $R_2$ and $R_2'$ form an oxo group; and wherein $R_3$ represents a hydrogen atom, or a methyl group, and wherein when $R_3$ represents a methyl group, the nitrogen atom bonded to $R_3$ is optionally in the form of an N-oxide. Alternatively such morphinan may be exogenously supplied to the cells.

In accordance herewith, the nucleic acid sequence encoding the codeine isomerase or codeinone reductase are linked to a nucleic acid sequence capable of controlling expression isomerase or codeinone reductase in a host cell. Accordingly, the present disclosure also provides a nucleic acid sequence encoding codeine isomerase and codeinone reductase linked to a promoter capable of controlling expression in a host cell. Nucleic acid sequences capable of controlling expression in host cells that may be used herein include any transcriptional promoter capable of controlling expression of polypeptides in host cells. Generally, promoters obtained from bacterial cells are used when a bacterial host is selected in accordance herewith, while a fungal promoter will be used when a fungal host is selected, a plant promoter will be used when a plant cell is selected, and so on. Further nucleic acid elements capable elements of controlling expression in a host cell include transcriptional terminators, enhancers and the like, all of which may be included in the chimeric nucleic acid molecules of the present disclosure. It will be understood by those ordinary skill in the art that operable linkage of nucleic acid sequences includes linkage of promoters and sequences capable of controlling expression to coding sequences in the 5' to 3' direction of transcription.

In accordance with the present disclosure, the chimeric nucleic acid molecules comprising a promoter capable of controlling expression in host cell linked to a nucleic acid sequence encoding codeine isomerase or a codeinone reductase, can be integrated into a recombinant expression vector which ensures good expression in the host cell. Accordingly, the present disclosure includes a recombinant expression vector comprising as operably linked components:

(i) a nucleic acid sequence capable of controlling expression in a host cell; and (ii) a nucleic acid sequence encoding a codeine isomerase or a codeinone reductase wherein the expression vector is suitable for expression in a host cell.

The term "suitable for expression in a host cell" means that the recombinant expression vector comprises the chimeric nucleic acid molecule of the present disclosure linked to genetic elements required to achieve expression in a host cell. Genetic elements that may be included in the expression vector in this regard include a transcriptional termination region, one or more nucleic acid sequences encoding marker genes, one or more origins of replication and the like. In preferred embodiments, the expression vector further comprises genetic elements required for the integration of the vector or a portion thereof in the host cell's genome, for example if a plant host cell is used the T-DNA left and right border sequences which facilitate the integration into the plant's nuclear genome.

Pursuant to the present disclosure the expression vector may further contain a marker gene. Marker genes that may be used in accordance with the present disclosure include all genes that allow the distinction of transformed cells from non-transformed cells, including all selectable and screenable marker genes. A marker gene may be a resistance marker such as an antibiotic resistance marker against, for example, kanamycin or ampicillin. Screenable markers that may be employed to identify transformants through visual inspection include β-glucuronidase (GUS) (U.S. Pat. Nos. 5,268,463 and 5,599,670) and green fluorescent protein (GFP) (Niedz et al., 1995, Plant Cell Rep., 14: 403).

One host cell that particularly conveniently may be used is *Escherichia coli*. The preparation of the *E. coli* vectors may be accomplished using commonly known techniques such as restriction digestion, ligation, gelectrophoresis, DNA sequencing, the Polymerase Chain Reaction (PCR) and other methodologies. A wide variety of cloning vectors are available to perform the necessary steps required to prepare a recombinant expression vector. Among the vectors with a replication system functional in *E. coli*, are vectors such as pBR322, the pUC series of vectors, the M13 mp series of vectors, pBluescript etc. Typically, these cloning vectors contain a marker allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium including but not limited to, Luria-Broth medium and harvested. Recombinant expression vectors may readily be recovered from cells upon harvesting and lysing of the cells. Further, general guidance with respect to the preparation of recombinant vectors and growth of recombinant organisms may be found in, for example: Sambrook et al., Molecular Cloning, a Laboratory Manual, Cold Spring Harbor Laboratory Press, 2001, Third Ed.

Further included in the present disclosure are a host cell wherein the host cell comprises a chimeric nucleic acid molecule comprising as operably linked components one or more nucleic acid sequences encoding a codeine isomerase or codeinone reductase. As hereinbefore mentioned, the host cell is preferably a host cell capable of producing the first morphinan, but not capable of naturally producing the second morphinan. In another embodiment, the host cell is able to produce the second morphinan, however the levels of second morphinan produced are lower than desirable and the levels of second morphinan are modulated relative to the levels of morphinan in the unmodified cells. In yet other embodiments, the cells are unable to naturally produce the first morphinan, and the first morphinan is provided to the cells as part of the cell's growth medium. Cells that may be used in accordance herewith include, without limitation, bacterial, yeast, or other fungal cells, plant cells, animal cells, or synthetic cells.

The present disclosure still further provides compositions comprising nucleic acid sequences encoding a polypeptide capable of, in a first morphinan having a mono-unsaturated $C_7$-$C_8$ bond and a saturated $C_8$-$C_{14}$ bond:
  (i) saturating the $C_7$-$C_8$ bond; and
  (ii) unsaturating the $C_8$-$C_{14}$ bond, to form a second morphinan having a saturated $C_7$-$C_8$ and a mono-unsaturated $C_8$-$C_{14}$ bond. In a preferred embodiment, the nucleic acid sequence is SEQ. ID NO: 1. In a further preferred embodiment, the nucleic acid sequence is SEQ. ID NO: 5.

In further aspects, the nucleic acid sequences encoding codeine isomerase, including the nucleic acid sequence set forth in SEQ. ID NO: 1, and the nucleic acid sequences encoding codeinone reductase, including the nucleic acid sequence set forth in SEQ. ID NO: 1, and SEQ. ID NO: 5, respectively, may be used to produce a cell that has modulated levels of expression of codeine isomerase or codeinone reductase. Such a cell is preferably a plant cell natively expressing codeine isomerase or codeinone reductase and, more preferably, a plant cell obtained from a plant belonging to the plant families Papaveraceae, Lauraceae, Annonaceae, Euphorbiaceae or Moraceae, and, most preferably, the plant belongs to the species *Papaver* somniferum, *Papaver* bracteatum, *Papaver* nudicale, *Papaver* orientale or *Papaver* rhoeas. Thus the present disclosure further provides a method for modulating expression of nucleic acid sequences in a cell naturally expressing codeine isomerase or codeinone reductase comprising:
  (a) providing a cell naturally expressing codeine isomerase or codeinone reductase;
  (b) mutagenizing the cell;
  (c) growing the cell to obtain a plurality of cells; and
  (d) determining if the plurality of cells comprises a cell comprising modulated levels of codeine isomerase or codeinone reductase.

In preferred embodiments, the method further comprises a step (e) as follows:
  (e) selecting a cell comprising modulated levels of codeine isomerase or codeinone reductase and growing such cell to obtain a plurality of cells.

In further preferred embodiments, plant seed cells are used to perform the mutagenesis. Mutagenic agents that may be used are chemical agents, including without limitation, base analogues, deaminating agents, alkylating agents, intercalating agents, transposons, bromine, sodium azide, ethyl methanesulfonate (EMS) as well as physical agents, including, without limitation, radiation, such as ionizing radiation and UV radiation. Thus the present disclosure further provides a method for producing a seed setting plant comprising modulated expression of nucleic acid sequences in a cell naturally expressing codeine isomerase or codeinone reductase, the method comprising:
  (a) providing a seed setting plant naturally expressing codeine isomerase or codeinone reductase;
  (b) mutagenizing seed of the plant to obtain mutagenized seed;
  (c) growing the mutagenized seed into the next generation mutagenized plants capable of setting the next generation seed; and
  (d) obtaining the next generation seed, or another portion of the mutagenized plants, and analyzing if the next generation plants or next generation seed exhibits modulated codeine isomerase expression or modulated codeinone reductase expression.

In preferred embodiments, a plurality of generations of plants and/or seed may be obtained, and portions of plants and/or seed in any or all of such generations may be analyzed. Analysis is typically performed by comparing expression levels (e.g. RNA levels or protein levels) in non-mutagenized (wild type) plants or seed with expression in mutagenized plants or seed. In further preferred embodiments, the analysis in step (d) may be performed by analyzing heteroduplex formation between wildtype DNA and mutated DNA. Thus in preferred embodiments, the analysing in step (d) comprises
  i. extracting DNA from mutated plants;
  ii. amplifying a portion of the DNA comprising a nucleic acid sequence encoding codeine isomerase or codeinone reductase to obtain amplified mutated DNA;
  iii. extracting DNA from wild type plants;

iv. mixing the DNA from wild type plants with the amplified mutated DNA and form a heteroduplexed polyucleotide;
v. incubating the heteroduplexed polynucleotide with a single stranded restriction nuclease capable of restricting at a region of the heteroduplexed polynucleotide that is mismatched; and
vi. determining the site of mismatch in the heteroduplex polynucleotide.

In preferred embodiments, the nucleic acid sequence encoding codeine isomerase that is used is set forth in SEQ. ID NO: 1.

In preferred embodiments, the nucleic acid sequence encoding codeinone reductase that is used is set forth in SEQ. ID NO: 5.

In further aspects, the nucleic acid sequences encoding codeine isomerase or codeinone reductase may be used to produce a cell that has modulated levels of expression of codeine isomerase or codeinone reductase by gene silencing. Thus the present disclosure further includes a method of reducing the expression of codeine isomerase or codeinone reductase in a cell, comprising:
(a) providing a cell expressing codeine isomerase or codeinone reductase; and
(b) silencing expression of codeine isomerase or codeinone reductase in the cell.

In preferred embodiments, the cell is a plant cell. Preferably, the plant is a member belonging to the plant families Papaveraceae, Lauraceae, Annonaceae, Euphorbiaceae or Moraceae, and more preferably, the plant belongs to the species *Papaver somniferum, Papaver bracteatum, Papaver nudicale, Papaver orientale* or *Papaver rhoeas*. A preferred methodology to silence codeine isomerase or codeinone reductase that is used is virus induced gene silencing (known to the art as VIGS). In general, in plants infected with unmodified viruses, the viral genome is targeted. However, when viral vectors have been modified to carry inserts derived from host genes (e.g. portions of sequences encoding codeine isomerase or codeinone reductase), the process is additionally targeted against the corresponding mRNAs. Thus the present disclosure further includes a method of producing a plant expressing reduced levels of codeine isomerase or codeinone reductase, the method comprising
(a) providing a plant expressing codeine isomerase or codeinone reductase; and
(b) reducing expression of codeine isomerase or codeinone reductase in the plant using virus induced gene silencing.

The hereinbefore mentioned methods to modulate expression levels of codeine isomerase or codeinone reductase may result in modulations in the levels of plant alkaloid morphinans, in plants including, without limitation, morphine, codeine, neopine. Thus the present disclosure includes the use of the methodologies to modify the levels of plant alkaloids in a plant naturally capable of producing plant alkaloids. Preferably, such plants belong to the plant families Papaveraceae, Lauraceae, Annonaceae, Euphorbiaceae or Moraceae, and more preferably, the plant belongs to the species *Papaver* somniferum, *Papaver* bracteatum, *Papaver* nudicale, *Papaver orientale* or *Papaver* rhoeas.

In yet further aspects of the present disclosure, the nucleic acid sequences encoding codeine isomerase or codeinone reductase may be used to genotype plants. Preferably, the plant is a member belonging to the plant families Papaveraceae, Lauraceae, Annonaceae, Euphorbiaceae or Moraceae, and more preferably, the plant belongs to the species *Papaver* somniferum, *Papaver* bracteatum, *Papaver* nudi-cale, *Papaver orientale* or *Papaver rhoeas*. In general, genotyping provides a means of distinguishing homologs of a chromosome pair and can be used to identify segregants in subsequent generations of a plant population. Molecular marker methodologies can be used for phylogenetic studies, characterizing genetic relationships among plant varieties, identifying crosses or somatic hybrids, localizing chromosomal segments affecting monogenic traits, map based cloning, and the study of quantitative inheritance. See, e.g., Plant Molecular Biology: A Laboratory Manual, Chapter 7, Clark, Ed., Springer-Verlag, Berlin (1997). For molecular marker methodologies, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7-21. The particular method of genotyping in accordance with the present disclosure may involve the employment of any molecular marker analytic technique including, but not limited to, restriction fragment length polymorphisms (RFLPs). RFLPs reflect allelic differences between DNA restriction fragments caused by nucleotide sequence variability. As is known to those of skill in the art, RFLPs are typically detected by extraction of plant genomic DNA and digestion of the genomic DNA with one or more restriction enzymes. Typically, the resulting fragments are separated according to size and hybridized with a nucleic acid probe. Restriction fragments from homologous chromosomes are revealed. Differences in fragment size among alleles represent an RFLP. Thus, the present disclosure further provides a means to follow segregation of a portion or genomic DNA encoding codeine isomerase or codeinone reductase, as well as chromosomal nucleic acid sequences genetically linked to these codeine isomerase or codeinone reductase encoding nucleic acid sequences using such techniques as RFLP analysis. Linked chromosomal nucleic sequences are within 50 centiMorgans (cM), often within 40 or 30 cM, preferably within 20 or 10 cM, more preferably within 5, 3, 2, or 1 cM of a genomic nucleic acid sequence encoding codeine isomerase or codeinone reductase. Thus, in accordance with the present disclosure the codeine isomerase or codeinone reductase encoding sequences of the present disclosure may be used as markers to evaluate in a plant population the segregation of nucleic acid sequences genetically linked thereto. Preferably, the plant population comprises or consists of plants belonging to the plant families Papaveraceae, Lauraceae, Annonaceae, Euphorbiaceae or Moraceae, and more preferably, the plant population comprises or consists of plants belonging to the species *Papaver somniferum, Papaver bracteatum Papaver nudicale, Papaver orientale* or *Papaver rhoeas*.

In accordance with the present disclosure, the nucleic acid probes employed for molecular marker mapping of plant nuclear genomes selectively hybridize, under selective hybridization conditions, to a genomic sequence encoding codeine isomerase or codeinone reductase. In preferred embodiments, the probes are selected from the nucleic acid sequences encoding codeine isomerase or codeinone reductase provided by the present disclosure. Typically, these probes are cDNA probes. Typically these probes are at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid plant chromosome complement. Some exemplary restriction enzymes employed in RFLP mapping are EcoRI, EcoRv, and Sstl. As used herein the term "restriction enzyme" includes reference to a composition that recognizes and, alone or in conjunction with another composition, cleaves a polynucleotide at a specific nucleotide sequence.

Other methods of differentiating polymorphic (allelic) variants of the nucleic acid sequences of the present disclosure can be used by utilizing molecular marker techniques well known to those of skill in the art, including, without limitation: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; and 6) allele-specific PCR. Other approaches based on the detection of mismatches between the two complementary DNA strands include, without limitation, clamped denaturing gel electrophoresis (CDGE); heteroduplex analysis (HA), and chemical mismatch cleavage (CMC). Thus, the present disclosure further provides a method of genotyping comprising the steps of contacting, under stringent hybridization conditions, a sample suspected of comprising a nucleic acid encoding codeine isomerase or codeinone reductase, with a nucleic acid probe capable of hybridizing thereto. Generally, the sample is a plant sample; preferably, a sample suspected of comprising a *Papaver somniferum* nucleic acid sequence encoding codeine isomerase or codeinone reductase (e.g., gene, mRNA). The nucleic acid probe selectively hybridizes, under stringent conditions, to a subsequence of the nucleic acid sequence encoding codeine isomerase or codeinone reductase comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a portion of a nucleic acid sequence encoding codeine isomerase or codeinone reductase.

Use of Morphinans

The morphinans obtained in accordance with the present disclosure may be formulated for use as a pharmaceutical drug, therapeutic agent or medicinal agent. Thus the present disclosure further includes a pharmaceutical composition comprising a morphinan prepared in accordance with the methods of the present disclosure. Pharmaceutical compositions comprising a morphinan in accordance with the present disclosure preferably further comprise vehicles, excipients and auxiliary substances, such as wetting or emulsifying agents, pH buffering substances and the like. These vehicles, excipients and auxiliary substances are generally pharmaceutical agents that may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, phosphates, sulfates, and the like; and the salts of organic acids such as acetates, propionates, benzoates, and the like. It is also preferred, although not required, that the preparation will contain a pharmaceutically acceptable excipient that serves as a stabilizer. Examples of suitable carriers that also act as stabilizers for peptides include, without limitation, pharmaceutical grades of dextrose, sucrose, lactose, sorbitol, inositol, dextran, and the like. Other suitable carriers include, again without limitation, starch, cellulose, sodium or calcium phosphates, citric acid, glycine, polyethylene glycols (PEGs), and combinations thereof. The pharmaceutical composition may be formulated for oral and intravenous administration and other routes of administration as desired. Dosing may vary and may be optimized using routine experimentation.

In further embodiments, the present disclosure provides methods for treating a patient with a pharmaceutical composition comprising a morphinan prepared in accordance with the present disclosure. Accordingly, the present disclosure further provides a method for treating a patient with a morphinan prepared according to the methods of the present disclosure, said method comprising administering to the patient a composition comprising a morphinan, wherein the morphinan is administered in an amount sufficient to ameliorate a medical condition in the patient.

EXAMPLES

Hereinafter are provided examples of specific embodiments for performing the methods of the present disclosure, as well as embodiments representing the compositions of the present disclosure. The examples are provided for illustrative purposes only, and are not intended to limit the scope of the present disclosure in any way.

Example 1—In Vitro Production of Neopine from Codeine

This example illustrates the in vitro production of neopine from codeine using codeine isomerase and codeinone reductase from *Papaver somniferum*.

E. coli cells were transformed with a nucleic acid sequence construct comprising SEQ. ID NO: 1 encoding a codeine isomerase having SEQ. ID NO:2, and or codeinone reductase comprising SEQ. ID NO: 5 encoding a codeinone reductase having SEQ. ID NO: 10. The polypeptide further was designed to comprise a histidine tag. Cells were grown and the codeine isomerase and codeinone reductase were isolated by affinity purification using the histidine tag. In order to assay for activity of the enzyme, codeine (15 µmol), NADP (1.8 µmol), and glycine buffer (1.8 mmol; pH 9.00) were incubated with the enzyme in a total volume of 10 mls under mild agitation at 30° C., before extraction at various time points (t=1 min; t=30 min; t=80 min and t=640 min) with two volumes (20 ml) of $CHCl_3$. The volume of the combined organic phase was reduced in vacuo and resolved using HPLC.

Figure 5:
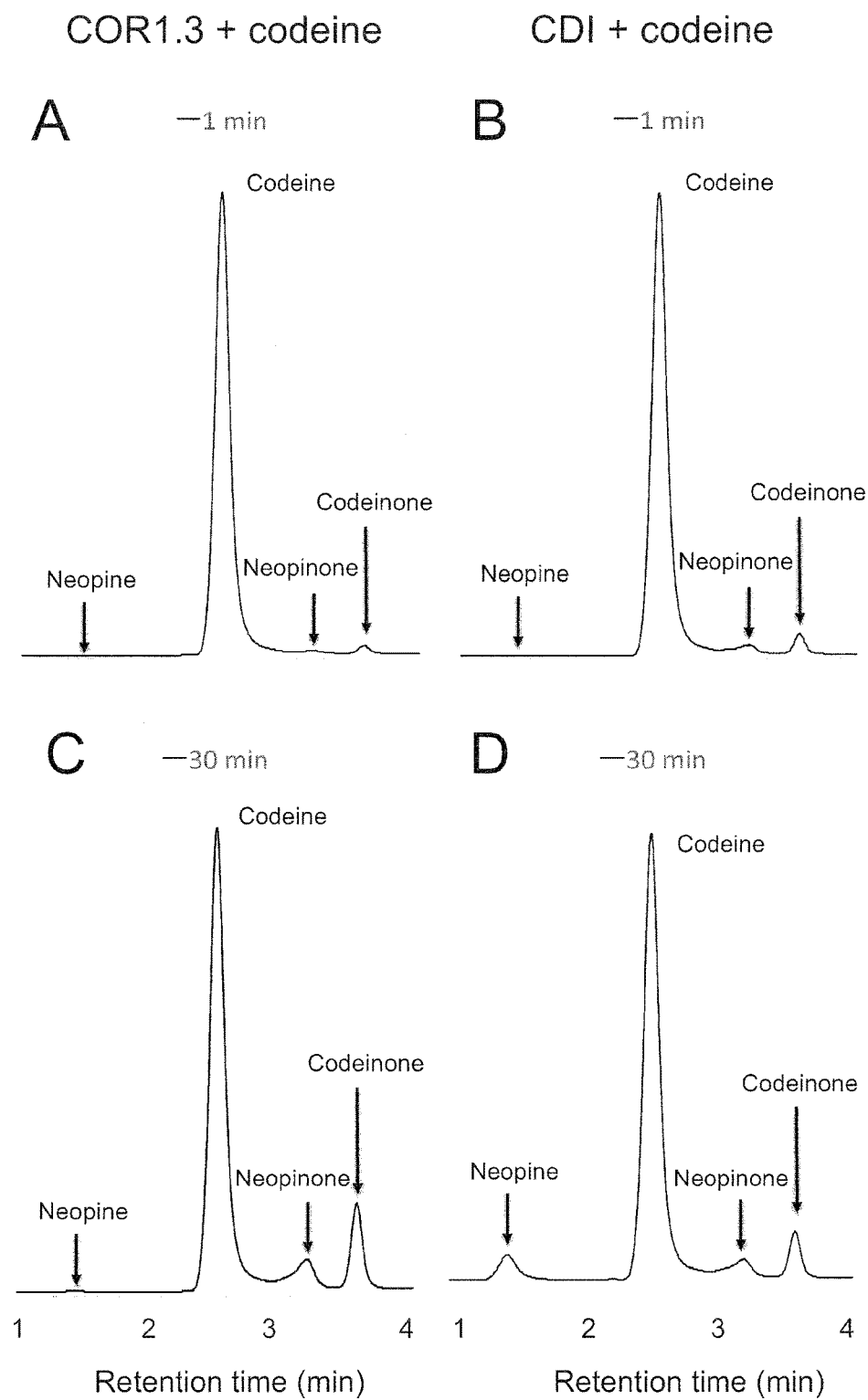
FIG. 5A and FIG. 5B depicts HPLC traces showing the in-vitro production of neopine from codeine using codeine isomerase. The reaction was performed for varying amounts of time (right hand panels; t=1 min (Panel A); t=30 mins (Panel C); t=80 min (Panel E) and t=640 mins (Panel G)). The control using codeinone reductase is shown in the left hand panels; t=1 min (Panel B); t=30 mins (Panel D); t=80 min (Panel F) and t=640 mins (Panel H).
Figure 5:
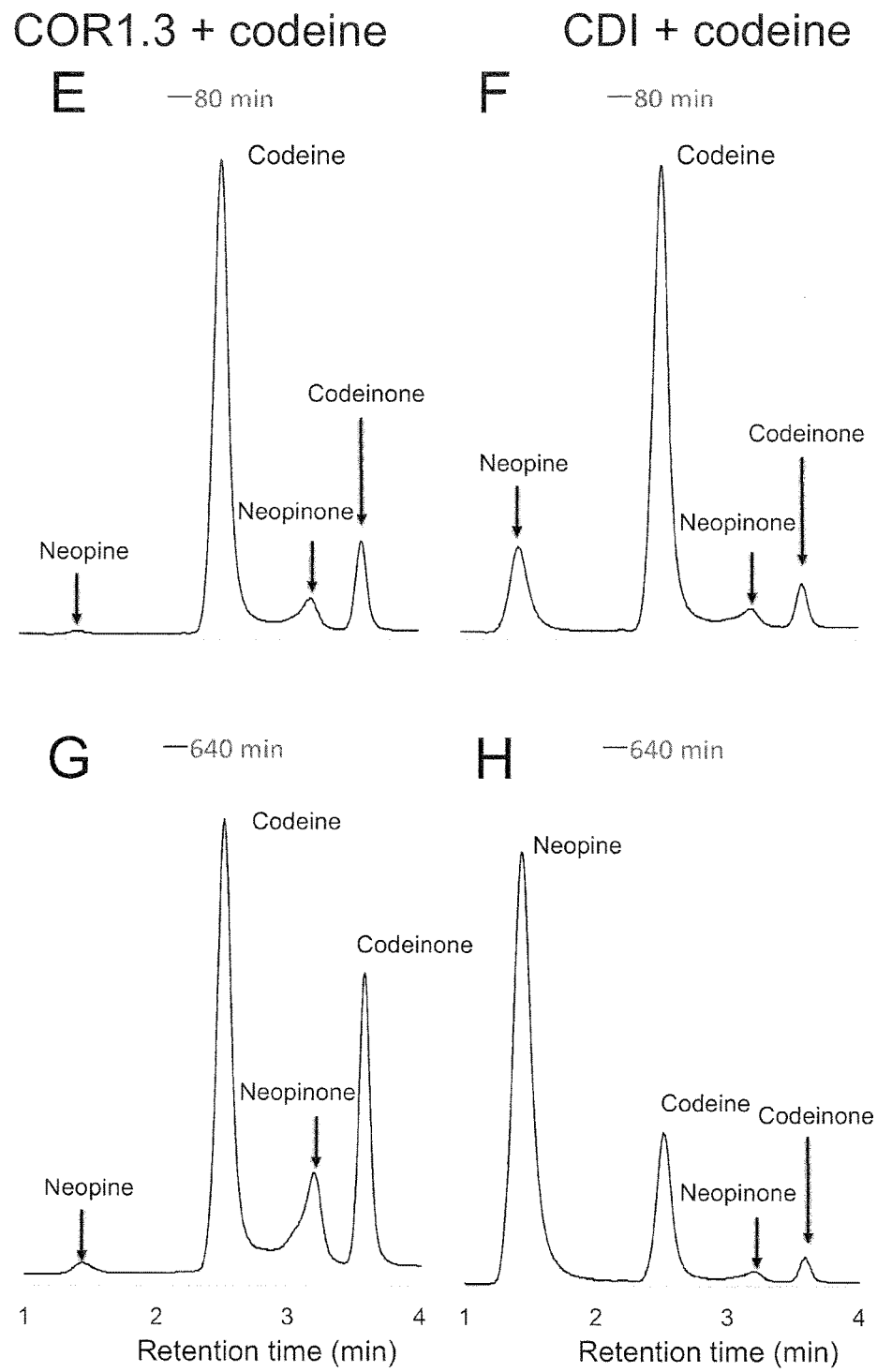

The results are shown in FIG. 5. It is noted that at retention time 1.5 mins, the codeine isomerase preparations yields substantial quantities of neopine, particularly following incubation for 640 mins. Smaller quantities of neopine were observed in the codeinone reductase preparations.

Example 2—In Vivo Production of Neopine in *E. coli*

This example illustrates the in vivo production in *E. coli* of neopine from codeine using codeine isomerase from *Papaver somniferum*.

Cloning of *Papaver somniferum* thebaine 6-O-demethylase (T6ODM) with Either COR1.3 or CDI—

Full-length coding region of T6ODM (SEQ. ID NO: 21) was amplified using Q5 Taq (NEB) with a FLAG sequence at the 5' end and subcloned into the E. coli expression vector pACE (MultiColi, Geneva-Biotech). CDI or COR1.3 were subcloned into the pACE vector using similar approach with a 5' His-tag sequence. The cassette of $T7_{pro}$-CDI-$T7_{ter}$ or $T7_{pro}$-CDI-$T7_{ter}$ was obtained via restriction digestion of the corresponding pACE construct using I-CeuI and BstXI enzymes. The construct of pACE-T6ODM was digested with only I-CeuI serving as the accepting vector. The insert, i.e. T7$_{pro}$-CDI-T7$_{ter}$ or T7$_{pro}$-CDI-T7$_{ter}$ was ligated into pACE-T6ODM using T4 DNA ligase (NEB). The final constructs were designated as pACE-T6ODM-CDI and pACE-T6ODM-COR1.3, which were then individually transformed into *E. coli* strain Rosetta (DE3) for expression. Expression of T6ODM, COR1.3 and CDI were confirmed by immunoblot analysis.

In Vivo Feeding Experiments—

Single colony of *E. coli* strain harboring pACE-T6ODM-CDI or pACE-T6ODM-COR1.3 was cultured in LB medium at 30° C. for overnight. Overnight cultures were inoculate in fresh LB medium to an OD$_{600}$ of 0.2 and grown until an OD$_{600}$ of 0.8 at 37° C. A 100 μl-aliquote of the individual cultures was then supplemented with 0.2 mM IPTG, 0.15 mM thebaine, 10 mM sodium ascorbate, 10 mM 2-oxoglutarate and 1.8 mM iron (II) sulfate and grown for 12, 24, 48 and 72 h. The supernatant was collected and diluted in methanol. An empty vector strain was used as a negative control.

LC-MS/MS Analysis—

Products in the culture medium derived from thebaine were analyzed using a 6410 Triple Quadruple LC-MS/MS (Agilent) for identification and quantification. Liquid chromatography was carried out using a Poroshell 120 SB C18 column (2.1×50 mm, 2.7 μm particle size; Agilent) at a flow rate of 0.6 mL min$^{-1}$. Liquid chromatography was initiated at 100% solvent A (10 mM ammonium acetate, pH5.5, 5% acetonitrile), ramped to 60% solvent B (acetonitrile) using a linear gradient over 8 min, further ramped to 99% solvent B using a linear gradient over 2 min, held constant at 99% solvent B for 1 min and returned to original conditions over 0.1 min for a 3 min equilibration period. Eluate was applied to the mass analyzer using an electrospray ionization probe operating in positive mode with the following conditions: capillary voltage, 4000 V; fragmentor voltage, 100 V; source temperature, 350° C.; nebulizer pressure, 50 PSI; gas flow, 10 L/min. For full-scan analysis, quadrupole 1 and 2 were set to RF only, whereas the third quadrupole scanned from 200-700 m/z. Positive-mode electrospray ionization (ESI [+]), collision-induced dissociation (CID) spectra were analyzed, the precursor m/z was selected in quadrupole 1 and collision energy of 30 eV was applied in quadrupole 2 and an argon collision gas pressure of 1.8×10$^{-3}$ torr. The resulting MS$^2$ fragments were resolved by quadrupole 3 scanning from 40 m/z to 2 m/z greater than the precursor ion m/z. Produce Compounds were identified based on retention times and ESI [+]-CID spectra compared with authentic standards or compared with previously published spectra.

Results—

Figure 7:
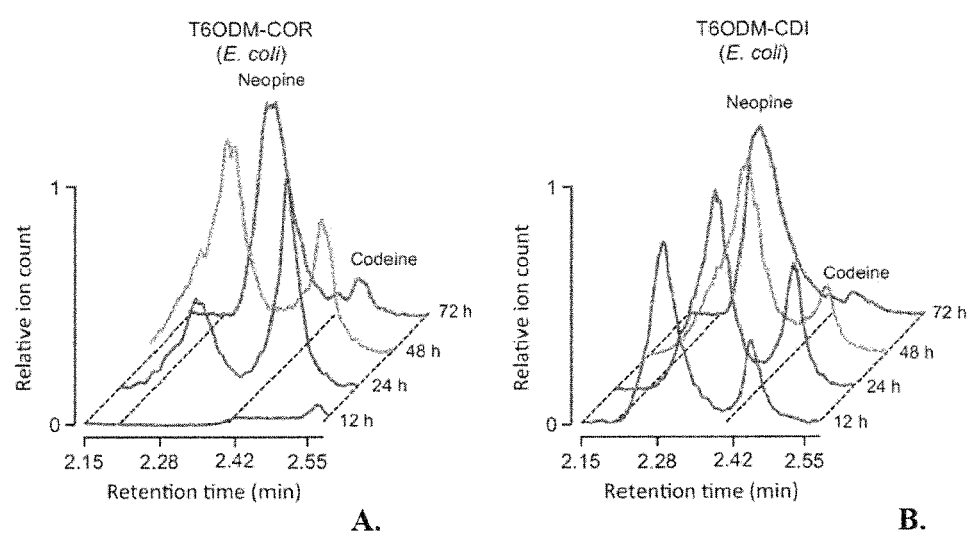
FIG. 7 depicts HPLC traces showing the in-vivo production of neopine in *E. coli* from codeine using codeinone reductase (FIG. 7A) and codeine isomerase (FIG. 7B). The reaction was performed for varying amounts of time (t=12 hours (blue); t=24 hours (green); t=48 hours (orange); and t=72 hours (red)).

Feeding thebaine to pACE-T6ODM-COR1.3 resulted in the formation of primarily codeine over 24-hour time course. After 24 h incubation until 72 h, neopine was the major product while the amount of codeine continued to decline (FIG. 7A). In contrast, feeding thebaine to pACE-T6ODM-CDI resulted in the formation of primarily neopine over the 72-hour time course (FIG. 7B).

Example 3—In Vivo Production of Neopine in Yeast

This example illustrates the in vivo production in yeast (*Saccharomyces cerevisiae*) of neopine from codeine using codeine isomerase from *Papaver* somniferum.

Cloning of *Papaver somniferum* thebaine 6 O-demethylase (T6ODM) with COR1.3 and CDI—

Full-length coding regions of T6ODM (see: SEQ. ID NO: 21), Gal10-Gal1 promoter region and PsCOR1.3 were amplified using PfuTurbo Hotstart DNA polymerase (Agilent). The PCR products were cloned to pCfB259 using the USER cloning system. The construct was designated pCfB259-T6ODM-COR1.3. Similarly, full-length coding regions of T6ODM, Gal10-Gal1 promoter region and CDI were amplified and cloned into pCfB259, and the construct was designated pCfB259-T6ODM-CDI. The two constructs were independently transformed into yeast strain CENPK102-5B and integrated to yeast chromosome. Expression of T6ODM, COR1.3 and CDI were confirmed by immunoblot analysis. The yeast strains were designated CENPK102-5B (T6ODM-COR1.3) and CENPK102-5B (T6ODM-CDI).

In Vivo Feeding Experiments—

Yeast strains CENPK102-5B (T6ODM-COR1.3) and CENPK102-5B (T6ODM-CDI) were cultured in SC growth medium (leucine dropout, 2% dextrose) and incubated at 30° C. for overnight. Cultures were then back-diluted 20× into SC medium (leucine dropout, 2% galactose) containing 200 μM thebaine and 50 mM 2-oxoglutarate (Sigma). Strains were grown for 12, 24, 48 and 72 h, and supernatant was collected and diluted in methanol. An empty vector strain was used as a negative control.

LC-MS/MS Analysis—

Products in the culture medium derived from thebaine were analyzed using a 6410 Triple Quadruple LC-MS/MS (Agilent) for identification and quantification. Liquid chromatography was carried out using a Poroshell 120 SB C18 column (2.1×50 mm, 2.7 μm particle size; Agilent) at a flow rate of 0.7 mL min$^{-1}$. Liquid chromatography was initiated at 100% solvent A (1% formic acid), ramped to 60% solvent B (acetonitrile) using a linear gradient over 6 min, further ramped to 99% solvent B using a linear gradient over 1 min, held constant at 99% solvent B for 1 min and returned to original conditions over 0.1 min for a 3.9 min equilibration period. Eluate was applied to the mass analyzer using an electrospray ionization probe operating in positive mode with the following conditions: capillary voltage, 4000 V; fragmentor voltage, 100 V; source temperature, 350° C.; nebulizer pressure, 50 PSI; gas flow, 10 L/min. For full-scan analysis, quadrupole 1 and 2 were set to RF only, whereas the third quadrupole scanned from 200-700 m/z. Positive-mode electrospray ionization (ESI [+]), collision-induced dissociation (CID) spectra were analyzed, the precursor m/z was selected in quadrupole 1 and collision energy of 30 eV was applied in quadrupole 2 and an argon collision gas pressure of 1.8×10$^{-3}$ torr. The resulting MS$^2$ fragments were resolved by quadrupole 3 scanning from 40 m/z to 2 m/z greater than the precursor ion m/z. Produce Compounds were identified based on retention times and ESI [+]-CID spectra compared with authentic standards or compared with previously published spectra.

Results—

Figure 8:
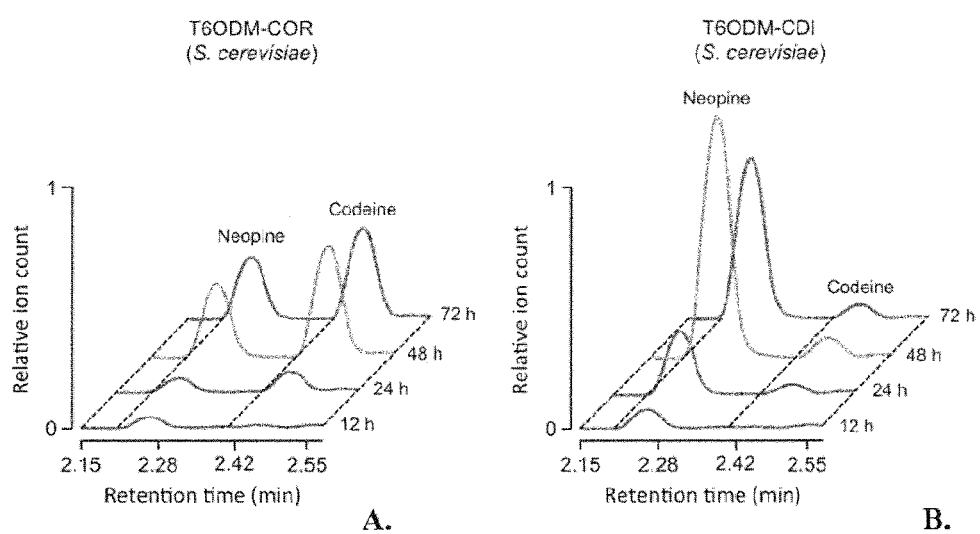
FIG. 8 depicts HPLC traces showing the in-vivo production of neopine in *S. cerevisiae* from codeine using codeinone reductase (FIG. 8A) and codeine isomerase (FIG. 8B). The reaction was performed for varying amounts of time (t=12 hours (blue); t=24 hours (green); t=48 hours (orange); and t=72 hours (red)).

Feeding thebaine to CENPK102-5B (T6ODM-COR1.3) resulted in the formation of codeine and neopine in similar quantities, slightly favoring the accumulation of codeine, over the 72-hour time course (FIG. 8A). In contrast, feeding thebaine to CENPK102-5B (T6ODM-CDI) resulted in the formation of primarily neopine over the 72-hour time course (FIG. 8B).

Example 4—Production of Neomorphine Using Morphine as a Substrate

This example illustrates the in vitro production of neomorphine from morphine using codeine isomerase from Papaversomniferum.

Codeine isomerase preparations were obtained from *E. coli* recombinantly expressing codeine isomerase, as described in Example 1. Morphine substrate was incubated with the enzyme, in the presence of NADPH and NADP$^+$ and the resulting reaction products were evaluated. In order to assay for activity of the enzyme, substrate (15 μmol), NADP (1.8 μmol), and glycine buffer (1.8 mmol; pH 9.00) were incubated with the enzyme in a total volume of 10 mls under mild agitation at 30° C., before extraction at time point t=640 min with two volumes (20 ml) of CHCl$_3$. The volume of the combined organic phase was reduced in vacuo and resolved using HPLC.

Figure 9:
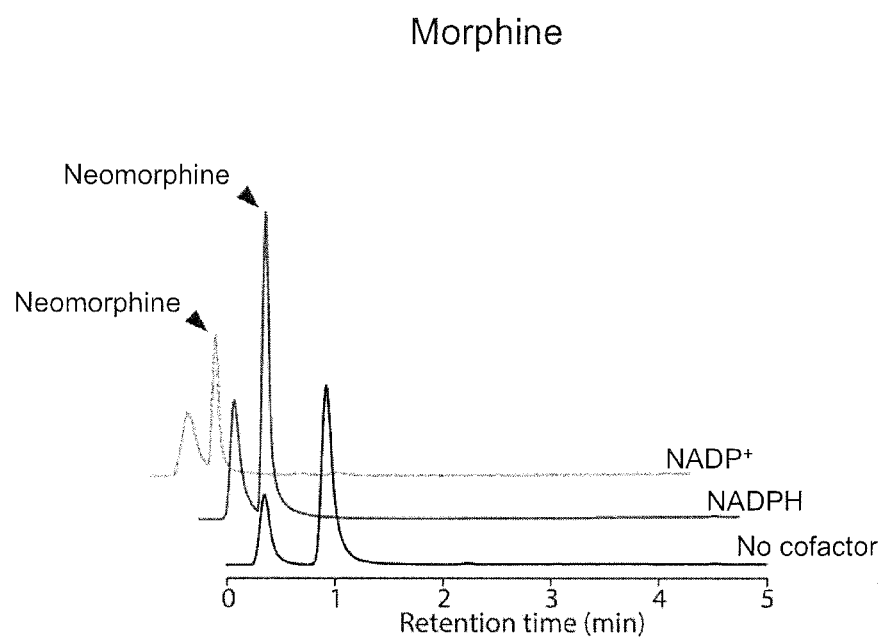
FIG. 9 depicts HPLC traces showing the in-vitro production of neomorphine from morphine using codeine isomerase in the presence of NADP+, NADPH and in the absence of co-factor.

The results are shown in FIG. 9.

Example 5—Production of Neopine Using Codeine as a Substrate

This example illustrates the in vitro production of neopine from codeine using codeine isomerase from Papaversomniferum.

Codeine isomerase preparations were obtained from *E. coli* recombinantly expressing codeine isomerase, as described in Example 1. Codeine-substrate was incubated with the enzyme, in the presence of NADPH and NADP$^+$ and the resulting reaction products were evaluated. In order to assay for activity of the enzyme, substrate (15 μmol), NADP (1.8 μmol), and glycine buffer (1.8 mmol; pH 9.00) were incubated with the enzyme in a total volume of 10 mls under mild agitation at 30° C., before extraction at time point t=640 min with two volumes (20 ml) of CHCl$_3$. The volume of the combined organic phase was reduced in vacuo and resolved using HPLC.

Figure 10:
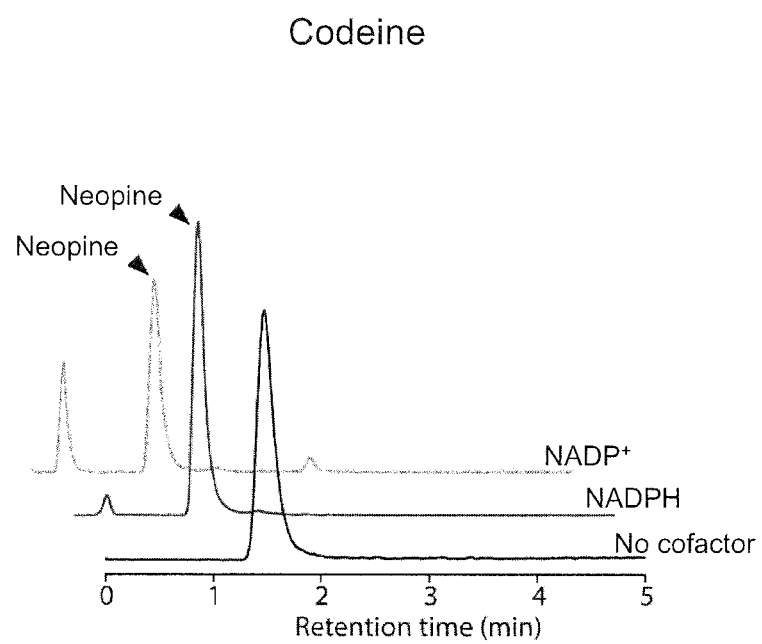
FIG. 10 depicts HPLC traces showing the in-vitro production of neopine from codeine using codeine isomerase in the presence of NADP+, NADPH and in the absence of co-factor.

The results are shown in FIG. 10.

Example 6—Production of Neomorphine N-Oxide Using Morphine N-Oxide as a Substrate This example illustrates the in vitro production of neomorphine N-oxide from morphine N-oxide using codeine isomerase from *Papaver somniferum*.

Codeine isomerase preparations were obtained from *E. coli* recombinantly expressing codeine isomerase, as described in Example 1. Morphine N-oxide substrate was incubated with the enzyme, in the presence of NADPH and NADP$^+$ and the resulting reaction products were evaluated. In order to assay for activity of the enzyme, substrate (15 μmol), NADP (1.8 μmol), and glycine buffer (1.8 mmol; pH 9.00) were incubated with the enzyme in a total volume of 10 mls under mild agitation at 30° C., before extraction at time point t=640 min with two volumes (20 ml) of CHCl$_3$. The volume of the combined organic phase was reduced in vacuo and resolved using HPLC.

Figure 11:
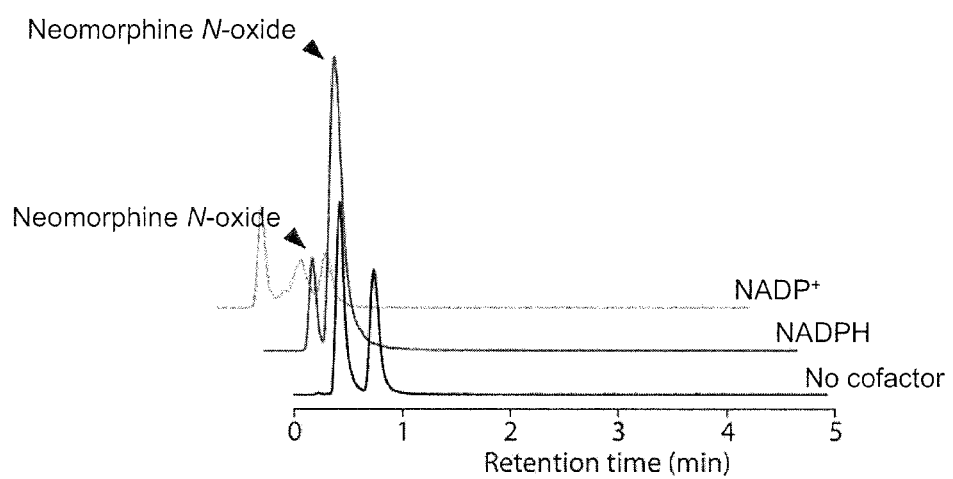
FIG. 11 depicts HPLC traces showing the in-vitro production of neomorphine N-oxide from morphine N-oxide using codeine isomerase in the presence of NADP+, NADPH and in the absence of co-factor.

The results are shown in FIG. 11.

Example 7—Production of Neopine N-Oxide Using Codeine N-Oxide as a Substrate

This example illustrates the in vitro production of neopine N-oxide from codeine N-oxide using codeine isomerase from *Papaver somniferum*.

Codeine isomerase preparations were obtained from *E. coli* recombinantly expressing codeine isomerase, as described in Example 1. Codeine N-oxide substrate was incubated with the enzyme, in the presence of NADPH and NADP$^+$ and the resulting reaction products were evaluated. In order to assay for activity of the enzyme, substrate (15 μmol), NADP (1.8 μmol), and glycine buffer (1.8 mmol; pH 9.00) were incubated with the enzyme in a total volume of 10 mls under mild agitation at 30° C., before extraction at time point t=640 min with two volumes (20 ml) of CHCl$_3$. The volume of the combined organic phase was reduced in vacuo and resolved using HPLC.

Figure 12:
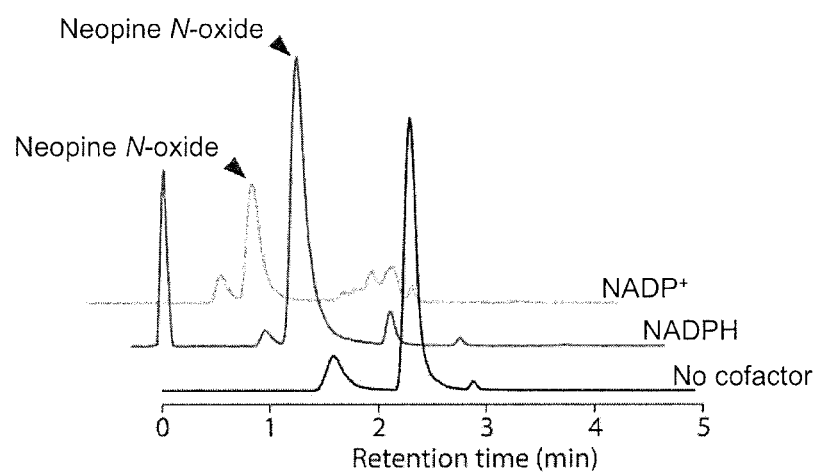
FIG. 12 depicts HPLC traces showing the in-vitro production of neopine N-oxide from codeine N-oxide using codeine isomerase in the presence of NADP+, NADPH and in the absence of co-factor.

The results are shown in FIG. 12.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

SUMMARY OF SEQUENCES

SEQ. ID NO: 1 and 2 set forth the nucleotide sequence and deduced amino acid sequence, respectively, of a codeine isomerase polypeptide of *Papaver* somniferum.

SEQ. ID NO: 3, 4, 5, 6 and 7 and SEQ. ID NO: 8, 9, 10, 11 and 12 set forth the nucleotide sequence and deduced amino acid sequence, respectively, of codeinone reductase polypeptides of *Papaver* somniferum.

SEQ. ID NO: 13; and SEQ. ID NO: 14 set forth the nucleotide sequence and deduced amino acid sequence, respectively, of a codeinone reductase polypeptide of *Papaver* rhoeas.

SEQ. ID NO: 15; and SEQ. ID NO: 16 set forth the nucleotide sequence and deduced amino acid sequence, respectively, of a codeinone reductase polypeptide of *Papaver* orientale.

SEQ. ID NO: 17; and SEQ. ID NO: 18 set forth the nucleotide sequence and deduced amino acid sequence, respectively, of a codeinone reductase polypeptide of *Papaver* nudicale.

SEQ. ID NO: 19; and SEQ. ID NO: 20 set forth the nucleotide sequence and deduced amino acid sequence, respectively, of a codeinone reductase polypeptide of *Papaver* bracteatum.

SEQ. ID NO: 21; and SEQ. ID NO: 22 set forth the nucleotide sequence and deduced amino acid sequence, respectively, of a 6-O-demethylase polypeptide of *Papaver* somniferum.

The invention claimed is:

1. A method of making a second morphinan having a $C_7$-$C_8$ saturated carbon bond and a $C_8$-$C_{14}$ mono-unsaturated carbon bond comprising:
   (a) providing a first morphinan having a $C_7$-$C_8$ mono-unsaturated carbon bond and a $C_8$-$C_{14}$ saturated carbon bond; and
   (b) contacting the first morphinan with a codeine isomerase or codeinone reductase capable of converting the first morphinan into the second morphinan;
   wherein
   the first morphinan has the chemical formula (V)

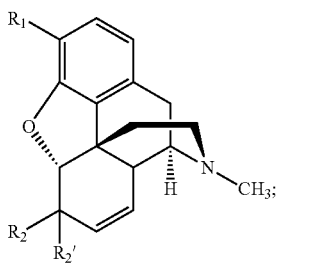

(V)

and wherein the second morphinan has the chemical formula (VI)

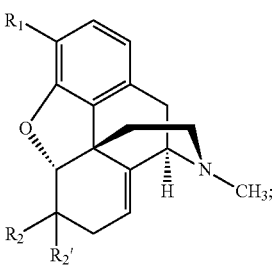

(VI)

and wherein in the first and second morphinan $R_1$ is a methoxy group, $R_2$ is a hydroxyl group and $R_2'$ a hydrogen atom;

or the first morphinan has the chemical formula (V)

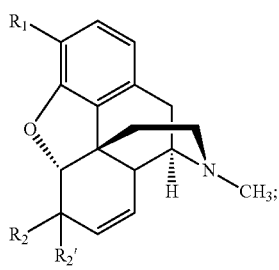

(V)

and wherein the second morphinan has the chemical formula (VI)

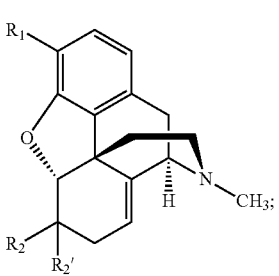

(VI)

and wherein in the first and second morphinan $R_1$ is a hydroxyl group, $R_2$ is a hydroxyl group and $R_2'$ is a hydrogen atom;

or
the first morphinan has the chemical formula (VII)

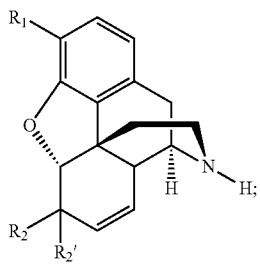
(VII)

and wherein the second morphinan has the chemical formula (VIII)

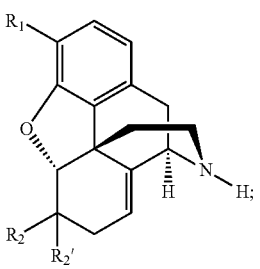
(VIII)

and wherein in the first and second morphinan R$_1$ is a methoxy group, R$_2$ is a hydroxyl group and R$_2$' is a hydrogen atom;

or
the first morphinan has the chemical formula (VII)

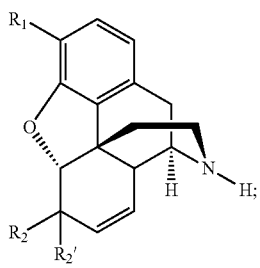
(VII)

and wherein the second morphinan has the chemical formula (VIII)

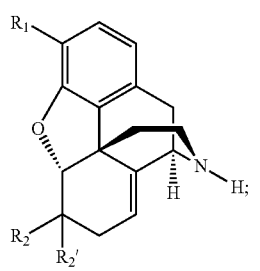
(VIII)

and wherein in the first and second morphinan R$_1$ is a hydroxyl group, R$_2$ is a hydroxyl group and R$_2$' is a hydrogen atom;

or
the first morphinan has the chemical formula (IX)

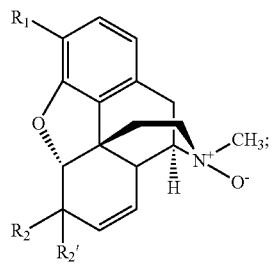
(IX)

and wherein the second morphinan has the chemical formula (X)

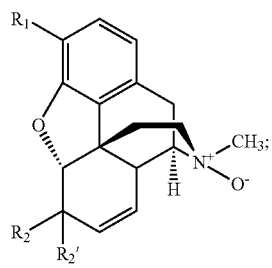
(X)

and wherein in the first and second morphinan R$_1$ is a methoxy group, R$_2$ is a hydroxyl group and R$_2$' is a hydrogen atom;

or
the first morphinan has the chemical formula (IX)

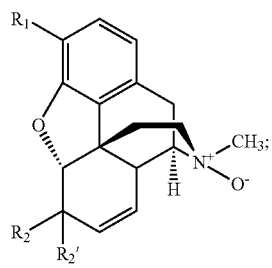
(IX)

and wherein the second morphinan has the chemical formula (X)

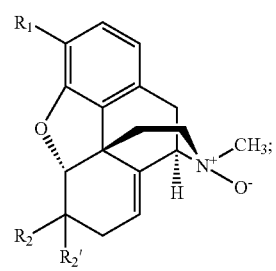
(X)

and wherein in the first and second morphinan R$_1$ is a hydroxyl group, R$_2$ is a hydroxyl group and R$_2$' is a hydrogen atom.

2. The method according to claim 1 further comprising a step (c) recovering the second morphinan.

3. A method for preparing a morphinan having chemical formula (II)

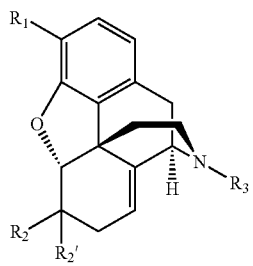
(II)

wherein, $R_1$ represents a hydroxyl group or a methoxy group; wherein $R_2$ represents a hydroxyl group and $R_2'$ represents a hydrogen atom; and wherein $R_3$ represents a hydrogen atom, or a methyl group, wherein when $R_3$ represents a methyl group, the nitrogen atom bonded to $R_3$ is optionally in the form of an N-oxide; and wherein the method comprises:
(a) providing a chimeric nucleic acid sequence comprising as operably linked components:
  (i) a nucleic acid sequence encoding a codeine isomerase polypeptide or codeinone reductase polypeptide;
  (ii) one or more nucleic acid sequences capable of controlling expression in a host cell;
(b) introducing the chimeric nucleic acid sequence into a host cell that endogenously produces or is exogenously supplied with a morphinan substrate;
(c) growing the host cell to produce codeine isomerase or codeinone reductase and to produce the morphinan having chemical formula (II); and
(d) recovering the morphinan having chemical formula (II) from the cell.

4. The method according to claim 3, wherein the nucleic acid sequence encoding the codeine isomerase comprises SEQ. ID. NO: 1 or a functional variant thereof, and wherein the nucleic sequence encoding the codeinone reductase comprises SEQ. ID NO: 5 or a functional variant thereof.

5. The method according to claim 3 wherein the cell is a bacterial cell, a yeast cell or a plant cell.

6. The method according to claim 3 wherein the morphinan substrate has the chemical formula (I)

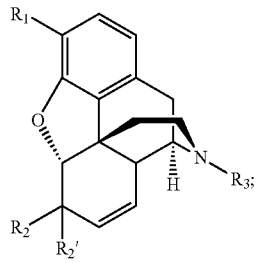
(I)

wherein in chemical formula (I), $R_1$ represents a hydroxyl group or a methoxy group; wherein $R_2$ represents a hydroxyl group and $R_2'$ represents a hydrogen atom; and wherein $R_3$ represents a hydrogen atom, or a methyl group, wherein when $R_3$ represents a methyl group, the nitrogen atom bonded to $R_3$ is optionally in the form of an N-oxide.

* * * * *